United States Patent
Shimokawa et al.

(10) Patent No.: US 10,578,518 B2
(45) Date of Patent: Mar. 3, 2020

(54) FILTER FAILURE DETECTION DEVICE AND PARTICULATE MATTER DETECTION DEVICE

(71) Applicant: DENSO CORPORATION, Kariya, Aichi-pref. (JP)

(72) Inventors: Hironobu Shimokawa, Nishio (JP); Kazuhiko Koike, Nishio (JP); Kensuke Takizawa, Nishio (JP); Manabu Yoshidome, Kariya (JP); Masayuki Tamura, Kariya (JP)

(73) Assignee: DENSO CORPORATION, Kariya (JP)

( * ) Notice: Subject to any disclaimer, the term of this patent is extended or adjusted under 35 U.S.C. 154(b) by 262 days.

(21) Appl. No.: 15/516,163

(22) PCT Filed: Oct. 2, 2015

(86) PCT No.: PCT/JP2015/078060
§ 371 (c)(1),
(2) Date: Mar. 31, 2017

(87) PCT Pub. No.: WO2016/052734
PCT Pub. Date: Apr. 7, 2016

(65) Prior Publication Data
US 2017/0307501 A1    Oct. 26, 2017

(30) Foreign Application Priority Data

Oct. 2, 2014 (JP) .................................. 2014-203771
Sep. 18, 2015 (JP) .................................. 2015-184870

(51) Int. Cl.
*G01M 15/10* (2006.01)
*G01N 15/02* (2006.01)
(Continued)

(52) U.S. Cl.
CPC ............ *G01M 15/102* (2013.01); *F01N 3/021* (2013.01); *F01N 11/007* (2013.01);
(Continued)

(58) Field of Classification Search
CPC ............. F01N 2560/05; F01N 2560/06; F02D 41/1494; F02D 41/1486; F02D 41/0235; G01N 15/0656; Y02T 10/48
See application file for complete search history.

(56) References Cited

U.S. PATENT DOCUMENTS

2011/0285410 A1    11/2011  Aoki et al.
2012/0031169 A1     2/2012  Sakamoto et al.
(Continued)

FOREIGN PATENT DOCUMENTS

DE    10 2013 105 741 A1    12/2013
JP         2012-052811        3/2012

OTHER PUBLICATIONS

Lee, Morphological Investigation of the Microstructure, Dimensions, and Fractal Geometry of Diesel Particulates, 2002, Engine and Emissions Research, Argonne National Laboratory (Year: 2002).*

*Primary Examiner* — Eric S. McCall
*Assistant Examiner* — Timothy P Graves
(74) *Attorney, Agent, or Firm* — Nixon & Vanderhye P.C.

(57) ABSTRACT

A control unit (6) estimates an output value of a PM sensor (S2) located at a downstream side of a DPF used as a reference filter, and detects whether the estimated output value exceeds a predetermined value (S3). When the estimated output value exceeds the predetermined value (YES in S3), the control unit detects an output value of the PM sensor (S4), and a heater heats the PM sensor (S5). The control unit detects an output value of the PM sensor (S6) after the PM sensor is heated, and calculates a change ratio of the output values of the PM sensor before and after (Continued)

heating (S7). The control unit estimates an average particle size of PM based on the calculated change ratio (S8), and detects whether the DPF has failed based on a comparison result of a corrected output value of the PM sensor with a threshold value.

13 Claims, 20 Drawing Sheets

(51) Int. Cl.
    *F02D 41/14* (2006.01)
    *F02D 41/02* (2006.01)
    *G01N 15/06* (2006.01)
    *G01N 1/22* (2006.01)
    *G01N 35/00* (2006.01)
    *G01N 27/04* (2006.01)
    *F01N 3/021* (2006.01)
    *F01N 11/00* (2006.01)
    *G01N 15/08* (2006.01)

(52) U.S. Cl.
    CPC ..... *F02D 41/0235* (2013.01); *F02D 41/1486* (2013.01); *F02D 41/1495* (2013.01); *G01N 1/2252* (2013.01); *G01N 15/0266* (2013.01); *G01N 15/0606* (2013.01); *G01N 15/0656* (2013.01); *G01N 15/0806* (2013.01); *G01N 27/04* (2013.01); *G01N 35/00613* (2013.01); *F01N 2550/04* (2013.01); *F01N 2560/05* (2013.01); *F01N 2560/06* (2013.01); *F01N 2560/20* (2013.01); *G01N 2015/0277* (2013.01); *G01N 2015/084* (2013.01); *Y02T 10/20* (2013.01); *Y02T 10/47* (2013.01); *Y02T 10/48* (2013.01)

(56) References Cited

U.S. PATENT DOCUMENTS

| | | |
|---|---|---|
| 2012/0144813 A1 | 6/2012 | Yahata et al. |
| 2012/0186330 A1 | 7/2012 | Ueno et al. |
| 2012/0260636 A1 | 10/2012 | Hashida et al. |
| 2013/0030678 A1* | 1/2013 | Aoki ............... F01N 9/002 701/113 |

* cited by examiner

FILTER FAILURE DETECTION DEVICE AND PARTICULATE MATTER DETECTION DEVICE

CROSS REFERENCE TO RELATED APPLICATIONS

This application is the U.S. national phase of International Application No. PCT/JP2015/078060 filed 2 Oct. 2015, which designated the U.S. and claims priority to JP Patent Application Nos. 2014-203771 filed 2 Oct. 2014, and 2015-184870 filed 18 Sep. 2015, the entire contents of each of which are hereby incorporated by reference.

TECHNICAL FIELD

The present invention relates to filter failure detection devices and particulate matter detection devices, the filter collects and accumulates particulate matter contained in exhaust gas emitted from an internal combustion engine, and the particulate matter detection device detects an amount of particulate matter contained in the exhaust gas.

BACKGROUND ART

There has been proposed a device for detecting an amount of particulate matter (PM) contained in exhaust gas emitted from an internal combustion engine (for example, see patent document 1.)

The patent document 1 has disclosed an electrical resistance type sensor which generates an output value corresponding to an amount of particulate matter contained in exhaust gas. Further, the patent document 1 has disclosed a method of correcting the output value of the electrical resistance type sensor on the basis of a temperature of exhaust gas, a temperature of this sensor and an amount of exhaust gas. This technique disclosed in the patent document 1 makes it possible to detect an amount of particulate matter with high accuracy without any influence due to the temperature of the sensor and the amount of exhaust gas.

CITATION LIST

Patent Literature

[Patent document 1] Japanese patent No. 5240679.

SUMMARY OF INVENTION

Technical Problem

However, according to the study of the inventors of the present invention, the inventors have found that an output value of the sensor greatly varies due to a particle size of particulate matter contained in exhaust gas emitted from an internal combustion engine. Because the technique disclosed in the patent document 1 does not consider the influence of particle size of particulate matter, it is difficult to suppress variation of the output value of the sensor due to the variation of the particle size of particulate matter. Further, when the sensor is arranged at a downstream side of the filter capturing particulate matter contained in exhaust gas, and a diagnosis of a filter failure is executed on the basis of a comparison result between the output value of the sensor and a threshold value, the diagnosis result varies due to the variation of the output value of the sensor.

The present invention has been made in consideration of the foregoing circumstances, and it is an object of the present invention to provide a filter failure detection device and a particulate matter detection device. The filter failure detection device suppresses diagnosis results of a filter failure from varying due to a particle size of particulate matter. The particulate matter detection device suppress an output value of a sensor from varying due to the particle size of particulate matter.

Solution to Problem

In order to achieve the object of the present invention, the filter failure detection device according to the present invention has a filter (4), a sensor (5), a particle size estimation section (6, 61, S4-S8, S24-S28, S44-S48, S64-S69, S85-S90, S104-S109, S125-S130, S144-S149, S165-S170), a failure detection section (6, S2, S3, S10-S12, S22, S23, S30-S32, S42, S43, S50-S52, S62, S63, S71-S73, S82, S83, S92-S94, S102, S103, S111-S113, S122, S123, S132-S134, S142, S143, S151-S153, S162, S163, S172-S174), and a correction section (S9, S29, S49, S70, S91, S110, S131, S150, S171). The filter is arranged in an exhaust passage (3) of an internal combustion engine (2), and captures and collects particulate matter contained in exhaust gas. The sensor is arranged in the exhaust gas pipe at a downstream side of the filter, and provides an output value which corresponds to an amount of particulate matter contained in exhaust gas. The particle size estimation section estimates an average particle size of particulate matter contained in exhaust gas. The failure detection section detects occurrence of a filter failure on the basis of a comparison result of the output value of the sensor and a threshold value. The correction section executes at least one of a sensor output correction and a threshold value correction. The sensor output correction corrects the output value of the sensor so that an amount of particulate matter increases according to reducing of the average particle size estimated by the particle size estimation section. The threshold value correction corrects the threshold value so that the amount of the particulate matter is reduced according to the reducing of the average particle size of particulate matter.

According to the study executed by the inventors of the present invention, there is a tendency in which the output of the sensor is reduced due to the reduction of an average particle size of particulate matter when an internal combustion engine emits exhaust gas which contains the same amount of particulate matter. The present invention has been made on the basis of the result of this study. The filter failure detection device according to the present invention estimates an average particle size of particulate matter, and executes at least one of the correction (sensor output correction) of an output value of the sensor on the basis of the estimated particle size of particulate matter, and the correction of the threshold value (threshold correction).

In the sensor output correction, because the output value of the sensor is adjusted so that an amount of particulate matter increases according to reducing of the average particle size of particulate matter, this makes it possible to approach the output value of the sensor when the average particle size of particulate matter is small to an output value of the sensor when the average particle size of particulate matter is large. That is, this makes it possible to suppress the output value of the sensor from varying due to the particle size of particulate matter.

In the threshold value correction, the threshold value is corrected so that the amount of particulate matter is reduced according to reduction of the average particle size of particulate matter. That is, this makes it possible to correct the threshold value on the basis of the variation of the output value of the sensor due to the particle size of particulate matter. As a result, this correction makes it possible to suppress influence of the particle size of particulate matter in view of the comparison of the output value of the sensor with the threshold value. As previously described, because the filter failure detection device according to the present invention executes at least one of the sensor output correction and the threshold value correction, it is possible to suppress variation of diagnosis results of the filter failure detection due to the particle size of particulate matter.

In addition, the particulate matter detection device according to the present invention has a sensor (5), a particle size estimation section (S4-S8, S44-S48, S64-S69, S85-S90, S144-S149, S165-S170, 61), a correction section (S9, S49, S70, S91, S150, S171). The sensor is arranged between an internal combustion engine (2) and an exhaust gas passage (3), and provides an output value which corresponds to an amount of particulate matter contained in exhaust gas. The particle size estimation section estimates an average particle size of particulate matter contained in the exhaust gas. The correction section corrects the output value of the sensor so that the amount of particulate matter increases according to reduction of the average particle size of particulate matter which has been estimated by the particle size estimation section.

According to the present invention, because the output value of the sensor is corrected so that the amount of particulate matter increases according to the reduction of the average particle size of particulate matter, it is possible to approach the output value of the sensor when the average particle size is small to the output value of the sensor when the average particle size is large. That is, this structure makes it possible to suppress the output value of the sensor due to variation of the particle size of particulate matter form varying.

DESCRIPTION OF EMBODIMENTS

Hereinafter, a description will be given of the filter failure detection device and the particulate matter detection device according to each of preferred exemplary embodiments of the present invention with reference to drawings.

First Exemplary Embodiment

Figure 1:
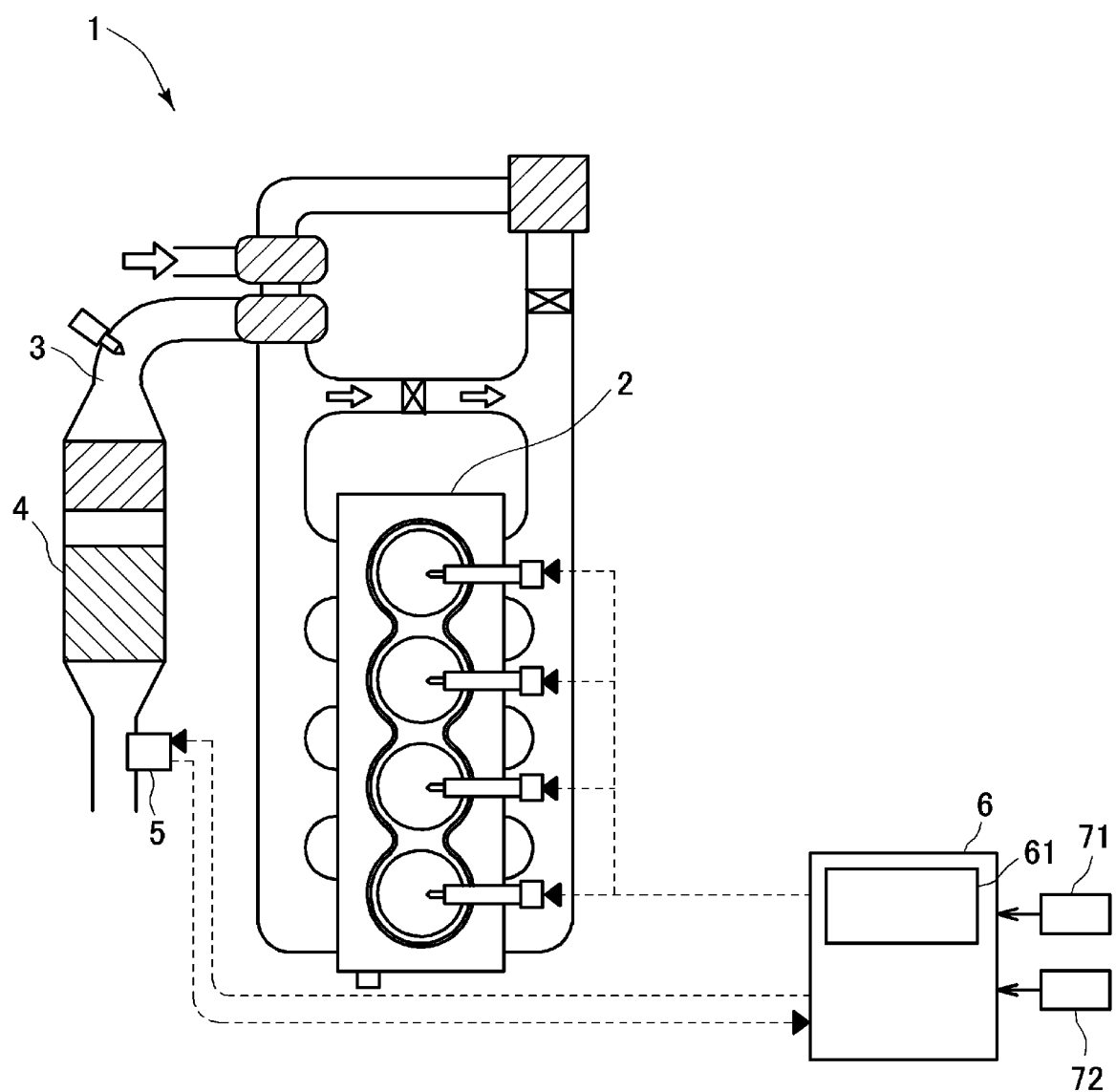
FIG. 1 is a view showing a structure of an engine system to which a filter failure detection device and a particle matter detection device according to the present invention are disposed.

FIG. 1 is a view showing a structure of an engine system 1 to which the filter failure detection device and the particle matter detection device according to the present invention are applied. As shown in FIG. 1, the engine system 1 is equipped with a diesel engine 2 (hereinafter, the engine 2 for short). The engine 2 has injectors for injecting fuel into a combustion chamber of the engine 1. The fuel injected by the injectors auto-ignites in the combustion chamber and generates power to move the vehicle.

A diesel particulate filter (DPF) 4 as the filter according to the present invention is arranged in an exhaust gas passage 3 of the engine 2. The DFP 4 is made of ceramic, and ha a known structure. For example, the DPF 4 has a honeycomb structure made of heat resistance ceramics such as cordierite. The DPF 4 has a plurality of cells through which exhaust gas flows. One of an inlet side and an outlet side of each of the cells is plugged so that the plugged inlet side and non-plugged inlet side of the cells are alternately arranged on an inlet side surface of the DPF 4, and the plugged inlet side and non-plugged inlet side of the cells are alternately arranged on an outlet-side surface of the DPF 4. The exhaust gas emitted from the engine 2 passes through partition walls of a porous structure of the cells in the DPF 4, and is discharged to the outside of the DPF 4. PM (particulate matter) contained in the exhaust gas is captured and collected by the partition walls of the porous structure of the cells.

A PM sensor 5 of an electrical resistance type as the sensor according to the present invention is arranged at a downstream side of the DPF 4. The PM sensor 5 detects an amount of PM contained in the exhaust gas.

Figure 2:
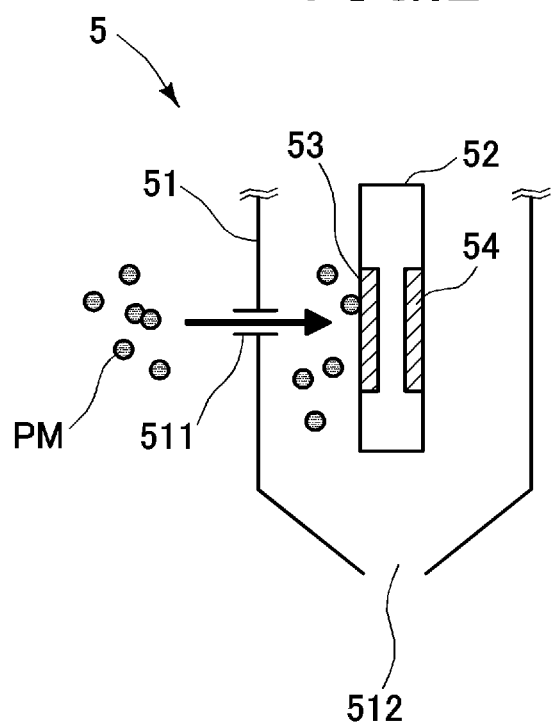
FIG. 2 is a view showing a schematic structure of a PM sensor used in FIG. 1.

FIG. 2 is a view showing a schematic structure of the PM sensor 5 used in FIG. 1. As shown in FIG. 2, the PM sensor 5 has a cylindrical cover 51 (hereinafter, the cover 51 for short) made of metal, for example, and the sensor element 52 arranged in the inside of the cover 51. Multiple holes 522 (i.e. exhaust gas introduction holes 511) are formed in the cover 51. A part of exhaust gas enters into the inside of the cover 51 through the exhaust gas introduction holes 511. Further, a discharge hole 512 is formed in the cover 51, through which the exhaust gas in the cover 51 is discharged to outside. FIG. 2 shows a structure in which the discharge hole 512 is formed at a front end of the cover 51.

The sensor element 52 is comprised of an insulation substrate made of ceramics, etc. A pair of opposing electrodes 53 are formed on one surface of the sensor element 52 (the insulation substrate). The opposing electrodes 53 are formed to separate from each other, and face to each other.

Figure 3:
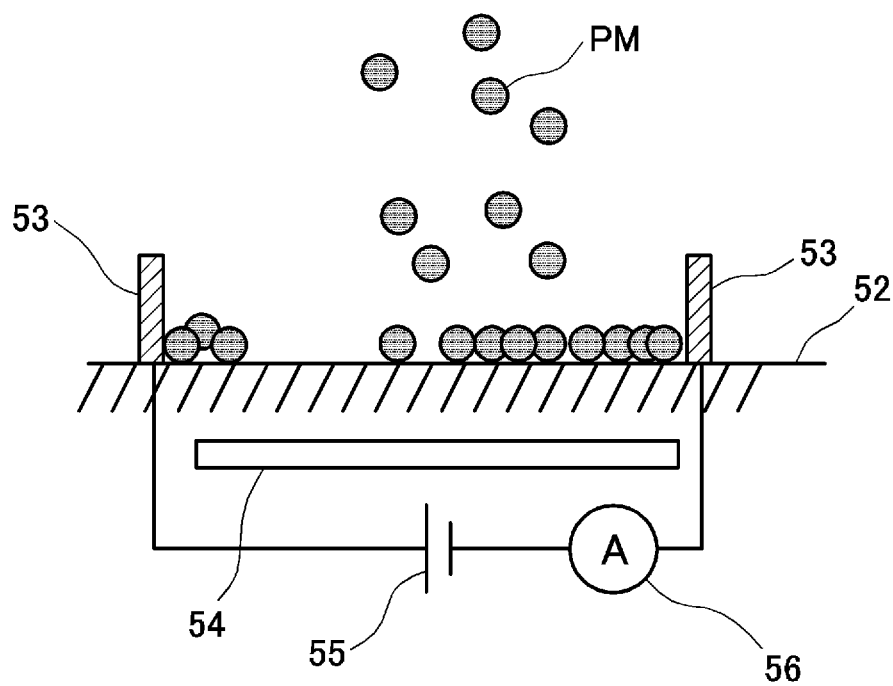
FIG. 3 is a view showing a partial section around a pair of opposing electrodes in a sensor element arranged in the PM sensor shown in FIG. 1 and explaining a detection principal to detect an amount of PM by the PM sensor.

FIG. 3 is a view explaining a detection principal to detect an amount of PM by the PM sensor 5, i.e., showing a partial section around the pair of the opposing electrodes 53 in the sensor element 51 arranged in the PM sensor 5 shown in FIG. 1. FIG. 3 shows PM captured by the area around the opposing electrodes 52. As shown in FIG. 3, a voltage supply circuit 55 is connected to the sensor element 52 so as to supply a predetermined direct current voltage to the pair of the opposing electrodes 53 on the basis of a control unit 6 which will be explained later. A part of exhaust gas which has introduced into the inside of the cover 51 is captured and collected by the sensor element 52 because PM itself has adhesiveness and adheres to the sensor element 52. Remaining PM which has not been captured is discharged to outside through the discharge hole 512.

When the voltage supply circuit 55 supplies the predetermined voltage to the opposing electrodes 33, one of the opposing electrodes 53 is positively charged, and the other thereof is negatively charged. This makes it possible to promote PM passing near the opposing electrodes 53 to be charged, and to promote the sensor element 52 to collect the PM. Hereinafter, a phrase "electrostatic collection" will be used, which represents the sensor element 52 collecting PM when the predetermined voltage is supplied to the opposing electrodes 53.

A description will now be given of the output characteristics of the PM sensor 5. A resistance between the opposing electrodes 53 varies due to an amount of PM collected by the sensor element 52. Accordingly, the PM sensor 5 generates and provides an output according to the amount of PM collected by the sensor element 52. That is, the PM sensor 5 provides the output which represents, as the amount of PM, the resistance value between the opposing electrodes 53. In more detail, when the sensor element 52 has a less amount of collected PM, the PM sensor 5 generates no output. (Strictly, the PM sensor 5 generates a small sensor output which is less than a threshold value which is used whether the output of the PM sensor 5 has risen. Because soot component contained PM is composed of carbon particles which have conductivity, a current starts to flow between the opposing electrodes 53, i.e., the output of the PM sensor 5 rises and the PM sensor 5 generates the output (which is not less than the threshold output) when the collected PM becomes not less than the predetermined amount.

After increase of the output of the PM sensor 5, because the resistance between the opposing electrodes 53 becomes more reduced according to increase of the amount of collected PM, the current flowing between the opposing electrodes 53 increases, i.e. the output of the PM sensor 5 becomes large. An ammeter 56 (see FIG. 3) is arranged in the engine system 1 so as to detect the current which is flowing between the opposing electrodes 53. A measured value of the ammeter 56 is the output of the PM sensor 5. For example, it is acceptable to detect a resistance value (or a voltage) between the pair of the opposing electrodes 53 and use the detected resistance as the output of the PM sensor 5 because there is a correlation between the current flowing between the opposing electrodes 53 and the resistance value between the opposing electrodes 53. The voltage supply circuit 55 and the ammeter 56 are arranged in the control unit 6 which will be explained later.

A heater 54 is formed in the sensor element 52, which generates heat energy to heat the sensor element 52. The heat energy of the heater 54 is used for regenerate the PM sensor 54. That is, PM collected by the sensor element 52 is completely burned to eliminate the PM from the sensor element 52. Further, the heater 54 is used for detecting an average particle size of PM (which will be explained later), in addition to regenerating of the PM sensor 5. For example, the heater 54 is arranged in the inside of the sensor element 52 on the other surface of the sensor element 52 (the insulation substrate), which is the opposing surface to that on which the electrodes 53 are formed. The heater 52 is composed of heating wires made of platinum (Pt) for example. In the regeneration of the PM sensor 5, the heater 54 is adjusted to generate heat energy so that a temperature of the sensor element 52 becomes not less than 600° C. (for example, at 700° C.), for example. The control unit 6, which will be explained later, is connected to the heater 54. The sensor element 52 corresponds to the adhesion section according to the present invention. The heater 54 corresponds to a heating section.

Returning to the explanation shown in FIG. 1, various types of sensors are mounted on the engine system 1, in addition to the PM sensor 5. These sensors are used for executing the operation of the engine 2. Specifically, the engine system 1 has a rotation sensor 71 detecting a rotation speed of the engine 2, an acceleration pedal sensor 72, etc. The acceleration pedal sensor 72 detects an operation amount (a depressed amount) of the acceleration pedal so as to provide a requested torque of the driver of the vehicle to the engine system 1.

Further, the engine system 1 has a control unit executing the overall control of the engine system 1. The control unit 6 is comprised of a computer system which is available on the commercial market. The computer system has a CPU (not shown) executing various types of arithmetic calculations, and a memory 61 storing various types of information. For example, the control unit 6 detects the operation state of the engine 2 on the basis of detection signals transmitted from the various types of sensors, and adjusts a fuel injection amount, an injection timing, an injection pressure, etc. to these optimum values, respectively, according to the operation state of the engine 2.

The control unit 6 has a function of controlling the operation of the PM sensor 5 in addition to the function of controlling the engine 2 previously described. In more detail, the control unit 6 is connected to the PM sensor 5, and controls a voltage supply of the voltage supply circuit 55 to execute the electrostatic collection of PM. Further, the control unit 6 controls the operation of the heater 54 to adjust a current amount and a voltage supply period of time so as to control the operation of the heater 54. This makes it possible to adjust a temperature of the heater 54 (a temperature of the sensor element 52).

Further, the control unit 6 executes the failure detection process which detects whether a DPF failure occurs on the basis of the detection value (a current value flowing between the opposing electrodes 53) of the PM sensor 5. A description will now be given of the failure detection process with reference to FIG. 4.

Figure 4:
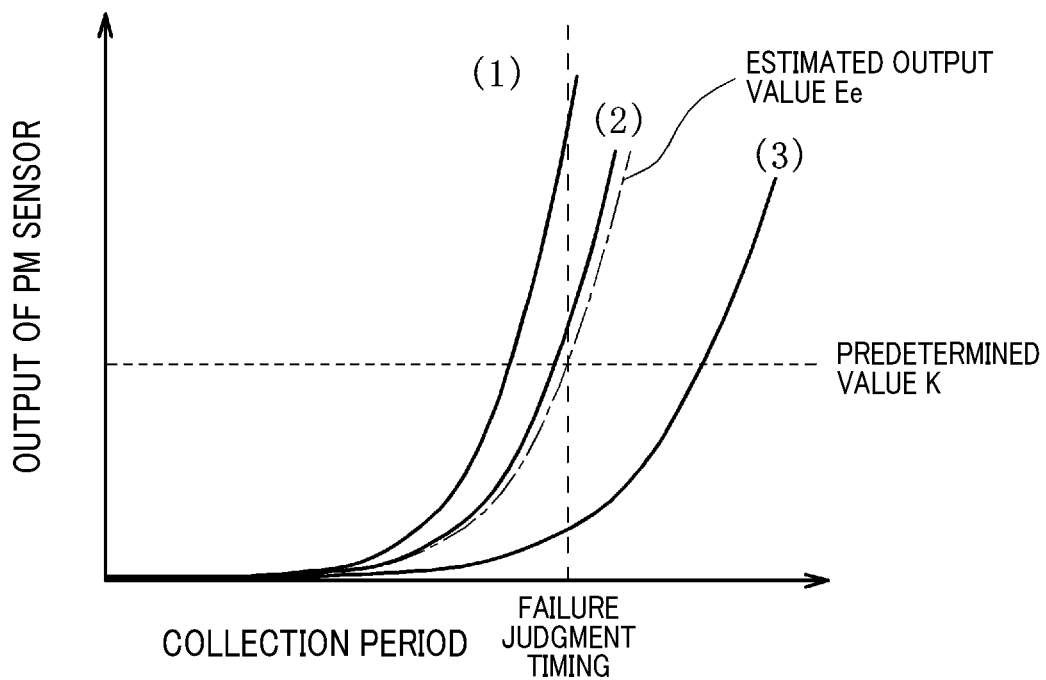
FIG. 4 is a view showing a variation of an output of the PM sensor according to a collection period of time.

FIG. 4 is a view showing a variation of the output of the PM sensor 5 according to the collection period of time counted from a start timing of the electrostatic collection. In more detail, the long dashed and short dashed line shown in FIG. 4 represents an estimated output value Ee of the PM sensor 5 when the DPF 4 is used as a reference filter to be used for detecting a failed DPF. The solid lines (1), (2) and (3) shown in FIG. 4 show actual output values of PM sensor 5.

In the present exemplary embodiment, so as to execute the failure detection of the DPF 4, an output value Ee of the PM sensor 5 is estimated when the DPF 4 is used as a reference filter so as to detect a failed DPF. The estimated output value Ee is used as a threshold value. It is possible to detect occurrence of a DPF failure on the basis of a comparison result between the output value of the actual PM sensor 5 and the threshold value (the estimated output value Ee). In more detail, when the output value of the actual PM sensor 5 is more than the threshold value (the estimated output value Ee), the detection result indicates that the DPF 4 has failed. On the other hand, when the output value of the actual PM sensor 5 is smaller than the threshold value, the detection result indicates that the DPF 4 is working correctly. In more detail, it is possible to use, as the threshold value, the estimated output value Ee (that is, the predetermined value K) at the timing (i.e. the failure detection timing) when the estimated output value Ee reaches the predetermined value K. When the output value of the actual PM sensor 5 is more than the threshold value K at the failure detection timing, it is judged that the DPF 4 has failed. When the output value of the actual PM sensor 5 is smaller than the threshold value K at the failure detection timing, it is judged that the DPF 4 is working correctly. In the example shown in FIG. 4, it is judged that the DPF 4 has failed when the output value of the actual PM sensor 5 is on the solid lines (1) and (2), and the DPF 4 is working correctly (is in a normal state) when the output value of the actual PM sensor 5 is on the solid line (3).

The Japanese patent NO. 5,115,873 has disclosed the processes of the failure detection process. In addition to the process, the present invention has disclosed an improved failure detection process as follows.

That is, the improved failure detection process estimates an rising timing (as a reference timing) when the output of the PM sensor 5 rises when the FPF 4 is used as the reference filter. Further, the improved failure detection process detects that the DPF 4 has failed when an actual rising timing (as an actual rising timing) of the output of the PM sensor 5 is before the reference timing. On the other hand, the improved failure detection process detects that the DPF 4 is working correctly when the actual rising timing of the output of the PM sensor 5 is after the reference timing.

On the other hand, as has been previously explained in the section [Solution to Problem], the output value of the PM sensor 5 significantly varies due to a particle size of PM even if an amount of PM emitted from the engine 2 is the same value. Specifically, the lines (1), (2) and (3) shown in FIG. 4 represent that the output values of the PM sensors when PM has a different particle size, respectively. As shown in FIG. 4, it can be recognized that the output value of the PM sensor significantly varies due to the change of the particle size of PM even if the amount of PM is the same. As a result, even if the amount of PM does not vary, it is detected that the PM sensor 5 has failed in the cases indicated by the lines (1) and (2) shown in FIG. 4. On the other hand, it is detected that the PM sensor 5 is working correctly in the case indicated by the line (3) shown in FIG. 4. That is, the incorrect detection of the failure detection process of the DPF 4 occurs due to the variation of the average particle size of PM.

Figure 5:
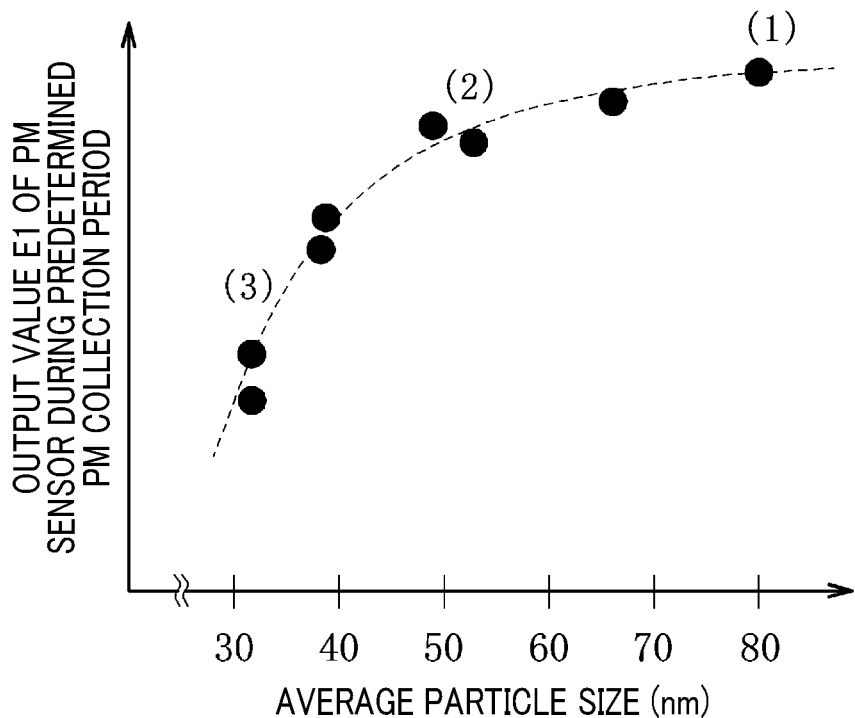
FIG. 5 shows experimental results which represent a relationship between an average particle size of PM and an output of the PM sensor.

FIG. 5 shows experimental results which represent a relationship between an average particle size of PM and an output of the PM sensor 5. Each of black points shown in FIG. 5 indicates an output E1 of the PM sensor 5 at a predetermined period of time (collection period of time) which is counted from a timing when the electrostatic collection starts, i.e. at a timing when the amount of PM collected by the PM sensor 5 is the same. Each of the black points (1), (2) and (3) shown in FIG. 5 indicates the output value of the PM sensor 5 at the predetermined period of time which corresponds to each of the lines (1), (2) and (3) shown in FIG. 4. The first exemplary embodiment uses the average particle size of PM which indicates a median diameter d50 of particle sizes of PM in an even cumulative distribution, in a PM particle size distribution, which have been measured by using an Engine Exhaust Particle Sizer (EEPS) Spectrometer manufactured by TSI Inc.

As shown in FIG. 5, the smaller the average particle size of PM, the smaller the output value of the PM sensor 5. In more detail, as shown in FIG. 5, the output value of the PM sensor 5 drastically varies due to the variation of the average particle size of PM in an area in which the average particle size of PM becomes smaller. FIG. 5 shows the variation of output value of the PM sensor 5 which has a convex output curve, which is due to the variation of the average particle size of PM. This indicates that PM is in an amorphous state with a low crystallization when having a small particle size. It can be considered that PM in an amorphous state (amorphous carbon) has a conductivity which is lower than a conductivity of PM in the graphite state.

In order to solve the problem previously described, the first exemplary embodiment estimates the average particle size of PM, and corrects the output value of the PM sensor 5 on the basis of the estimated average particle size of PM, and executes the failure detection process of the DPF 4.

A description will now be given of the failure detection process of the DPF 4 executed by the control unit 6.

Figure 6:
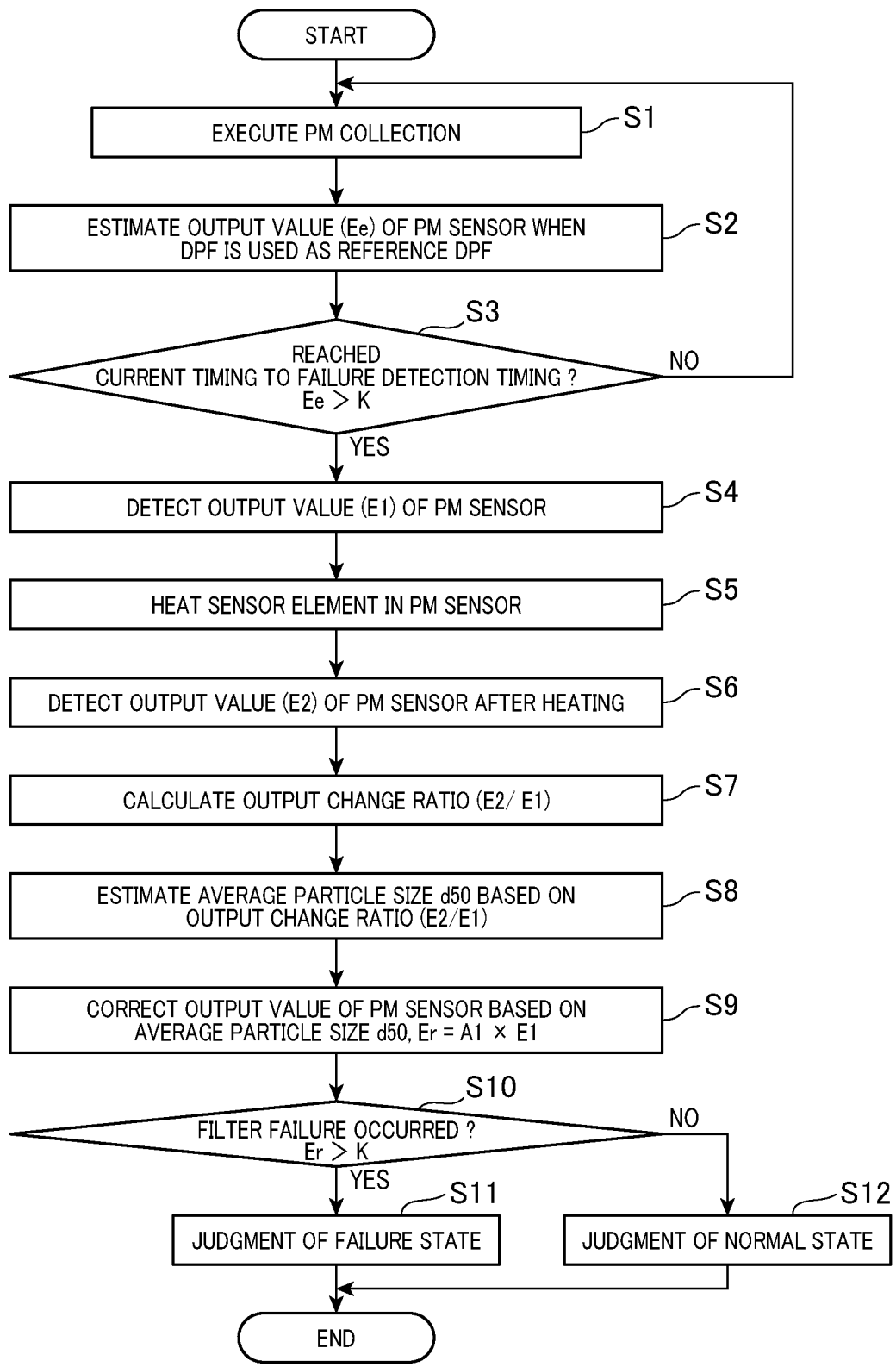
FIG. 6 is a view showing a flow chart of a failure detection process according to a first exemplary embodiment.

FIG. 6 is a view showing a flow chart of the failure detection process according to the first exemplary embodiment. For example, the control unit 6 starts to execute the failure detection process shown in FIG. 6 at a timing immediately when the engine 2 starts to operate, and repeatedly executes the failure detection process until a timing when the engine 2 stops operating. The PM sensor 5 does not collect any PM at the start timing of the failure detection process shown in FIG. 6.

When starting the failure detection process shown in FIG. 6, the control unit 6 instructs the voltage supply circuit 55 (see FIG. 3) to supply a voltage between the opposing electrodes 53. This starts the execution of the electrostatic collecting of PM (step S1). The PM sensor 5 starts to collect PM contained in exhaust gas, i.e. starts the PM collection process.

Next, the control unit 6 estimates the output value Ee of the PM sensor 5 when the DPF 4 is used as the reference DPF on the basis of the operation state of the engine 2 (step S2). That is, the control unit 6 estimates the long dashed and short dashed line shown in FIG. 4. Specifically, the first exemplary embodiment uses the reference DPF which is the DPF 4 under a failure state having a low collecting rate, in which an amount of PM contained in exhaust gas passed through and discharged from the DPF 4 corresponds to a regulation value of the failure self-diagnosis (On-Board-Diagnostic, i.e. OBD in short). This OBD regulation value is greater than an EM regulation value (Exhaust gas regulation value) such as EURO 6, etc. For example, in a specific drive mode, when the amount of PM as the EM regulation value is 4.5 mg/km, the control unit 6 uses the OBD regulation value which is the amount of PM of 12.0 mg/km which is approximately 2.67 times the EM regulation value.

Specifically, in step S2, the control unit 6 estimates the amount f of PM at each timing (per unit time) which passes through the DPF 4 when the DPF 4 is the reference DPF on the basis of the operation state of the engine 2. The control unit 6 calculates an accumulated amount B of the amount f of PM at each estimated timing. Specifically, similar to the method disclosed in the Japanese patent No. 5,115,873, the control unit 6 estimates an amount of PM emitted from the engine 2, in other words, an amount of inflow PM (or inflow amount of PM) which flows into the reference DPF on the basis of the operation state of the engine 2 such as a rotation speed and a torque (a fuel injection amount) of the engine 2. It is possible to obtain the rotation speed of the engine 2 on the basis of signals transmitted from a rotation speed sensor 71, and to obtain the torque (the fuel injection amount) on the basis of signals transmitted from an acceleration pedal sensor 72 and the rotation speed of the engine 2. A map which represents a relationship between the operation state (rotation speed, torque, etc.) of the engine 2 and an amount of inflow PM has been stored in the memory 61 (see FIG. 1). It is acceptable to read the amount of inflow PM which corresponds to the operation state of the engine 2 from the map.

The control unit 6 estimates a PM collection rate of the reference DPF. Specifically, the control unit 6 uses a predetermined value a as the PM collection rate of the reference DPF, for example. Because the PM collection rate of a DPF varies due to an accumulation amount of PM collected in the DPF or a flow amount of exhaust gas, it is possible to correct the PM collection rate a on the basis of the accumulation amount of PM and the flow amount of exhaust gas. For example, it is sufficient to estimate the accumulation amount of PM on the basis of a difference in pressure between a point before the DPF 4 and a point after the DPF 4. Further, it is also possible to estimate the flow amount of exhaust gas on the basis of an amount of fresh air detected by an air flow meter (not shown) which detects an intake amount of fresh air introduced into the engine 2. In this case, the control unit 6 estimates the flow amount of exhaust gas while considering an expansion amount of exhaust gas corresponding to a temperature of exhaust gas detected by an exhaust gas temperature sensor (not shown), and a compressed part of exhaust gas which corresponds to a pressure detected by a pressure sensor (not shown).

The amount f of PM (an amount of outflow PM) per unit time which flows out from the reference DPF is obtained on the basis of the estimated amount of inflow PM and the estimated PM collection rate of the reference DPF. It is possible to obtain the accumulation amount B of PM at the downstream side of the DPF 4 at a current timing (i) by adding the amount f of outflow PM to the accumulation amount B previously estimated at the timing (i−1).

Next, the control unit 6 estimates an amount of PM, collected by the PM sensor 5, in the obtained accumulation amount B of PM. Specifically, the control unit 6 estimates a PM collection rate $\beta$ by the PM sensor 5 while considering an amount of PM, wherein exhaust gas containing PM is introduced into the inside of the cover 51 through the exhaust gas introduction holes 511 (see FIG. 2), from the overall amount of PM which flows outside of the PM sensor 5, and an amount of PM, to be adhered on the sensor element 52, from the overall amount of Pm entered inside of the cover 51. It is acceptable to use a predetermined constant value as the PM collection rate $\beta$ regardless of various states, such as an a flow amount of exhaust gas, an excess air rate $\lambda$, a temperature of exhaust gas, a temperature of the sensor element 52, etc.

It is also acceptable to use a corrected value as the as the PM collection rate $\beta$ according to various types of conditions. For example, the more the amount of exhaust gas increases, the less the amount of PM enters the inside of the cover 51, and the less the amount of PM entered inside of the cover 51 is adhered on the sensor element 52. In this case, there is a tendency of easily detaching PM adhered on the sensor element 52 from the surface of the sensor element 52. In addition, the smaller the excess air rate $\lambda$, the larger an amount of PM which is not collected by the Pm sensor 5. Accordingly, for example, the larger the flow amount of exhaust gas, or the smaller the excess air rate $\lambda$, the more the control unit 6 reduces the estimated PM collection rate $\beta$. Further, because the thermophoresis force to be applied to the sensor element 52 varies due to a temperature of exhaust gas and a temperature of the sensor element 52, the PM collection rate $\beta$ also varies. Accordingly, the amount of PM collected by the PM sensor 5 is obtained on the basis of the accumulation amount B of PM and the PM collection rate $\beta$.

Because the output value of the PM sensor 5 increases according to the increasing of the amount of collected PM, the control unit 6 detects in advance a relationship between the amount of collected PM and the output value of the PM sensor 5, and stores the relationship into the memory 61. It is therefore possible for the control unit 6 to obtain the estimated output value of the PM sensor 5 on the basis of the relationship stored in the memory 61 and the currently detected amount of PM under the case which uses the DPF 4 as the reference DPF.

Because the larger the accumulation amount B of PM, the larger the output value of the PM sensor 5, the relationship between the accumulation amount B of PM and the output value of the PM sensor 5 is detected in advance and stored in the memory 61. It is acceptable for the control unit 6 to estimate the output value of the PM sensor 5 on the basis of the currently-obtained accumulation amount B of PM and the relationship stored in the memory 61.

Next, the control unit 6 detects whether the output value Ee of the PM sensor 5, which has been estimated in step S2, exceeds the predetermined value K (see FIG. 4), and judges whether or not the time has been reached to reach to execute the failure detection of the DPF 4 (failure detection timing) (step S3). This predetermined value K is set to a value at which the output of the PM sensor 5 rises, for example. That is, the process in step S3 detects whether the output of the PM sensor 5 has reached the timing at which the output of the PM sensor 5 rises when the DPF 4 is used as the reference DPF.

In step S3, when the detection result indicates that the output of the PM sensor 5 does not reach the failure detection timing, that is, the output value Ee of the PM sensor 5 is less than the predetermined value K ("NO" in step S3), the operation flow returns to step S1. In step S3, the control unit 6 continues the PM collection and the estimation of the output value Ee of the OM sensor 5.

Figure 7:
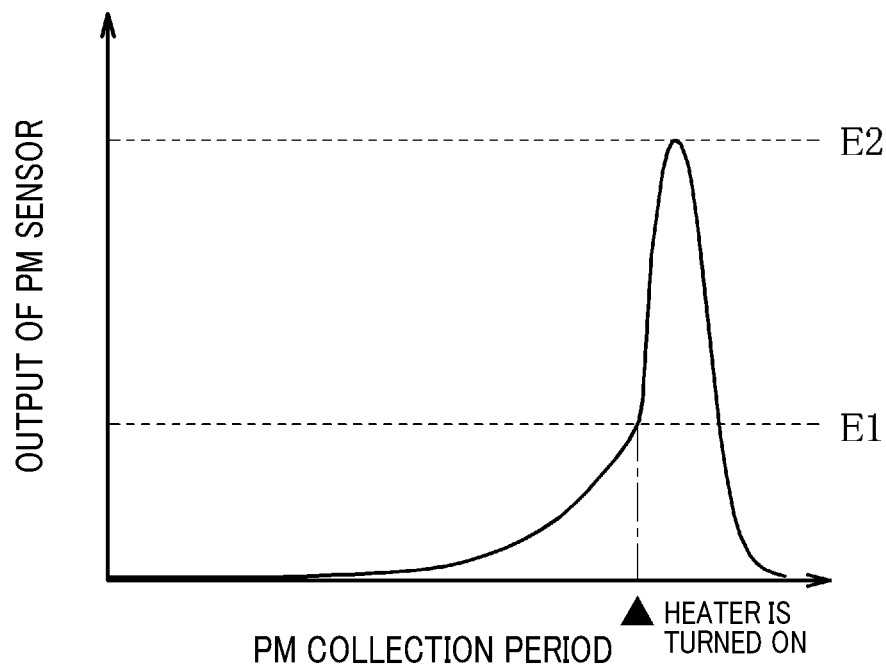
FIG. 7 is a view showing variation of the output of the PM sensor according to the collecting period of time of PM before or after heating of the PM sensor.
Figure 8:
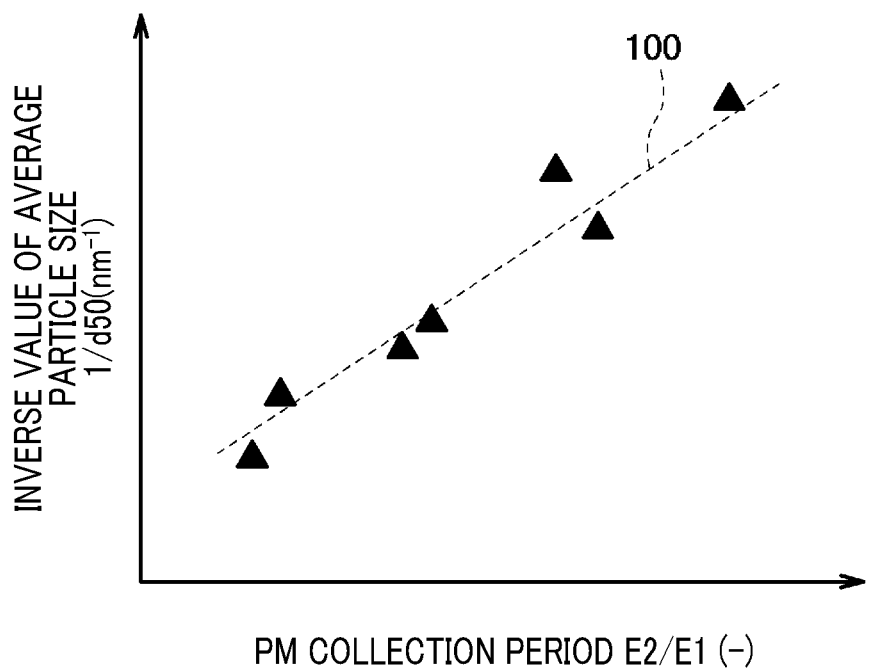
FIG. 8 is a view showing a relationship between an output change rate and an average particle size of PM according to the first exemplary embodiment, a second exemplary embodiment and a third exemplary embodiment.

When the detection result indicates that the output of the PM sensor 5 reaches the failure detection timing, that is, the output value Ee of the PM sensor 5 has exceeded the predetermined value K ("YES" in step S3), the operation flow progresses to step S4. In step S4 to step S8, the control unit 6 estimates an average particle size d50 (median diameter) of PM contained in exhaust gas. FIG. 7 and FIG. 8 are views explaining the method of estimating the average particle size d50 of PM. In more detail, FIG. 7 shows a variation of the output of the PM sensor 5 which corresponds to the collection period of time before and after the heating process of the sensor element 52. FIG. 8 shows a relationship between a change rate of the output of the PM sensor 5 and the average particle size d50 of PM before and after the heating process of the sensor element 52. In FIG. 8, the vertical axis indicates a reverse value of the average particle size d50, and each point represents an experimental result by using the EEPS Spectrometer previously described.

Next, a description will be given of the method of estimating the average particle size d50 of PM with reference to FIG. 7 and FIG. 8. As shown in FIG. 7, when the sensor element 52 is heated by using heat energy generated by the heater 54, the output of the PM sensor 5 gradually increases according to the increasing of the temperature of the sensor element 52. This means that the PM collected by the sensor element 52 is heated by the increasing of the temperature of the sensor element 52, a crystallization of the collected PM varies, and the conductivity of the collected PM increases. That is, the collected PM is changed from an amorphous state to a graphite state having a high conductivity. When the PM sensor 5 before heating generates the output E1 (see FIG. 7), and generates the peak output value E2 (see FIG. 7) after heating, the output change rate E2/E1 correlates with the average particle size d50.

Specifically, as shown in FIG. 8, the output change rate E2/E1 has a positive correlation (a proportional relation) with an inverse value of the average particle size d50. That is, the larger the output change rate E2/E1, the smaller the average particle size d50 (the larger the inverse value of the average particle size d50). When the particle size of PM becomes small, the Pm enters in an amorphous state. Because the PM has a low conductivity, the change rate of the conductivity of the PM in graphite state increased. As shown in FIG. 7, the smaller the particle size of PM, the smaller the output value E1 of the PM sensor 5 before heating. On the other hand, the particle size of PM after heating approximately does not change. Accordingly, the smaller the particle size of PM, the larger the output change rate E2/E1.

The relationship 100 shown in FIG. 8 is detected and stored in the memory 61 as a memory section according to the present invention. In step S4 to step S8 shown in FIG. 6, the control unit 6 estimates the average particle size d50 on the basis of the relationship 100 and the output change rate E2/E1 currently detected. That is, the control unit 6 detects the output value E1 (the output value before heating) of the PM sensor 5 before the sensor element 52 is heated by the heater 54 (step S4).

Next, the heater 54 generates heat energy to heat the sensor element 52 (step S5). It is acceptable to heat the sensor element 52 at a temperature (which is more than 600° C.) which executes combustion of PM, or a temperature (approximately 400° C.) which does not execute the combustion of PM. FIG. 7 shows a case in which the sensor element 52 is heated at the temperature which executes the combustion of PM. For this reason, the output of the PM sensor 5 increases according to increasing of the temperature of the sensor element 52, and is then reduced after the output value E2 of the PM sensor 5 because PM has been burned. That is, during a period counted from a heating start timing to the timing of the output value E2 of the PM sensor 5, the sensor element 52 has the temperature at which no PM is burned. After the period of the peak output value E2 of the PM sensor 5, the sensor element 52 has the temperature at which PM is burned.

If the sensor element 52 is heated to a temperature at which no PM is burned, the output value of the PM sensor 5 does not reduce and is maintained at the peak output value E2.

Next, the control unit 6 detects the peak value E2 (the output value after heating) of the PM sensor 5 which has risen by heating the sensor element 52 (step S6). Specifically, for example, it is acceptable to detect the peak value E2 by monitoring the output of the PM sensor 5 from the timing when the heat process has started, or detect the output value of the PM sensor 5 as the peak value at the timing which has been determined to represent the peak value of the PM sensor 5/. The output value E2 of the PM sensor 5 detected in step S6 represents the output value of the PM sensor 5 at a temperature (for example, 400° C.) at which no PM is burned. It is possible to easily distinguish the output change ratio E2/E1 when PM has a small particle size and the output change ratio E2/E1 when PM has a large particle size.

Next, the control unit 6 calculates the output change ratio E2/E1 (a change rate of the output value E2 after heating to the output value E1 before heating) (step S7) between the output value E1 of the PM sensor 5 detected in step S4 and the output value E2 of the PM sensor 5 detected in step S6.

Next, the control unit 6 estimates the average particle size d50 (step S8) on the basis of the relationship shown in FIG. 8 and the output change ratio E2/E1 calculated in step S7. The average particle size d50 obtained by the process in step S8 represents the average particle size of PM which has been discharged at the downstream side of the DPF 4 during the period counted from the timing when the electrostatic collection is started by the process in step S1 to the timing at which the process in step S3 detects the occurrence of the failure detection timing.

Figure 9:
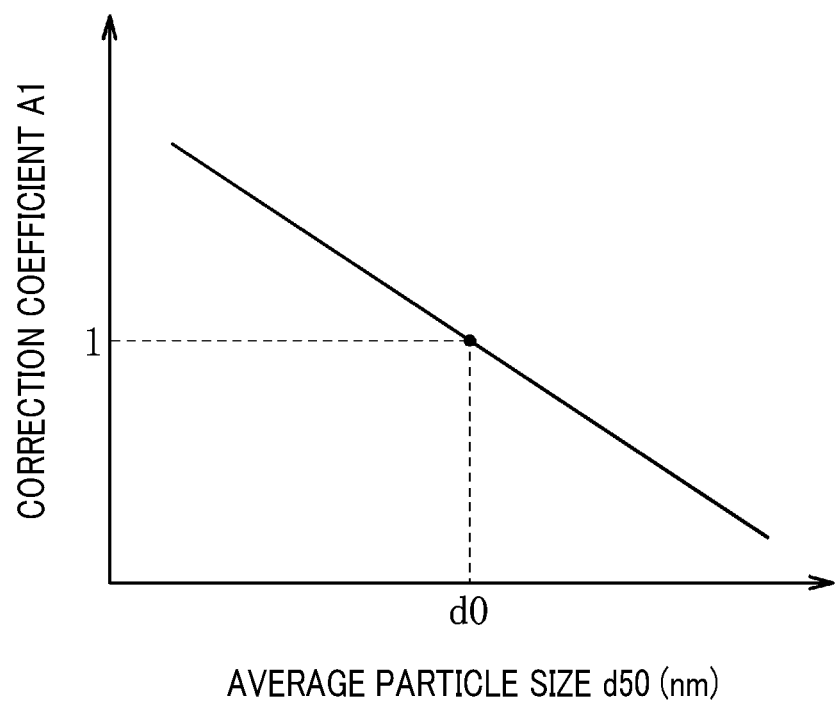
FIG. 9 is a view showing a relationship between the average particle size of PM and the output of the PM sensor.

Next, the control unit 6 corrects the output value E1 (the output value before heating) of the PM sensor 5 (step S9) detected in step S4 on the basis of the average particle size d50 which has been estimated in step S8. Specifically, as shown in FIG. 9, the control unit 6 stores the relationship (map) between the average particle size d50 and a correction coefficient A1 of the output of the PM sensor 5 into the memory 61. In the relationship shown in FIG. 9, the smaller the average particle size d50, the more the correction coefficient A1 increases. FIG. 9 shows the proportional relationship between the average particle size d50 and the correction coefficient A1. However, there is another possible relationship designated by a convex curve upward or a concave curve downward. Further, the correction coefficient A1 has a value of 1 when the average particle size d50 has a predetermined reference value d0 (for example, 60 nm), the correction coefficient A1 has a value of more than 1 when the average particle size d50 is smaller than the predetermined reference value d0, and the correction coefficient A1 has a value of less than 1 when the average particle size d50 is larger than the predetermined reference value d0. In other words, it is determined to have the correction coefficient A1 so that the corrected output value of the PM sensor 5 becomes the output value of the PM sensor 5 when the average particle size d50 has the predetermined reference value d0.

In step S9, the control unit 6 calculates the correction coefficient A1 on the basis of the relationship shown in FIG. 9 and the average particle size d50 which has been estimated in step S8. The control unit 6 calculates the output value Er of the PM sensor 5 after correction by multiplying the output value E1 of the PM sensor 5 and the correction coefficient A1 together. That is, the control unit 6 executes the calculation of Er=A1×E1. This calculation makes it possible to correct the output value of the Pm sensor 5 so that the amount of PM increases, i.e. has a large value according to the reduction of the average particle size d50. Further, this calculation makes it possible to approach the output value Er of the PM sensor 5 after correction to the output value of the PM sensor at the reference value d0, i.e. when the average particle size d50 has the predetermined reference value d0.

Next, the control unit 6 detects whether the output value Er of the PM sensor 5 after correction obtained in step S9 is larger or not than the predetermined value K (see FIG. 4). The predetermined value K is the estimated output value Ee at the failure detection timing (step S10).

When the detection result in step S10 indicates that the output value Er of the PM sensor 5 is larger than the predetermined value K ("YES" in step S10), the control unit 6 detects that the DPF 4 has failed, which has a DPF collection capability which is lower than that of the reference DPF (step S11). On the other hand, when the detection result in step S10 indicates that the output value Er of the PM sensor 5 is not more than the predetermined value K ("NO" in step S10), the control unit 6 detects that the DPF 4 is working s correctly (is in a normal state), which has the DPF collection capability which is higher than that of the reference DPF (step S12).

After the process in step S11 or S12, the control unit 6 finishes the process of the flow chart shown in FIG. 6.

As previously described, the filter failure detection device and the particle matter detection device according to the first exemplary embodiment estimates the average particle size of PM and corrects the output value of the PM sensor on the basis of the estimated average particle size of PM. This makes it possible to suppress the output of the PM sensor 5 from varying due to the influence of the average particle size of PM. Further, because the filter failure detection device and the particle matter detection device executes the failure detection process of a DPF on the basis of the output value of the PM sensor, the variation of which has been suppressed, it is possible to suppress the judgment results from varying. That is, this makes it possible to avoid an incorrect judgment of detecting that a DPF has failed in spite of the fact that the DPF is working correctly, or to avoid an incorrect judgment of detecting that the DPF is working correctly in spite of the fact that the DPF has failed.

The inventors according to the present invention have found that there is the correlation between the output change ratio E2/E1 of the PM sensor by heating and the average particle size of PM (see FIG. 8). Because the filter failure detection device and the particle matter detection device according to the first exemplary embodiment estimates the average particle size of PM on the basis of the correlation previously described, it is possible to detect the average particle size of PM contained in exhaust gas with high accuracy.

Second Exemplary Embodiment

Next, a description will now be given of the failure detection process according to the second exemplary embodiment of the present invention. Hereinafter, a difference between the second exemplary embodiment and the first exemplary embodiment will be mainly explained. In the second exemplary embodiment, the control unit 6 executes the failure detection process which is different in process from that of the first exemplary embodiment. Other processes of the second exemplary embodiment are the same as those in the first exemplary embodiment. A description will now be given of the failure detection process according to the second exemplary embodiment.

Figure 10:
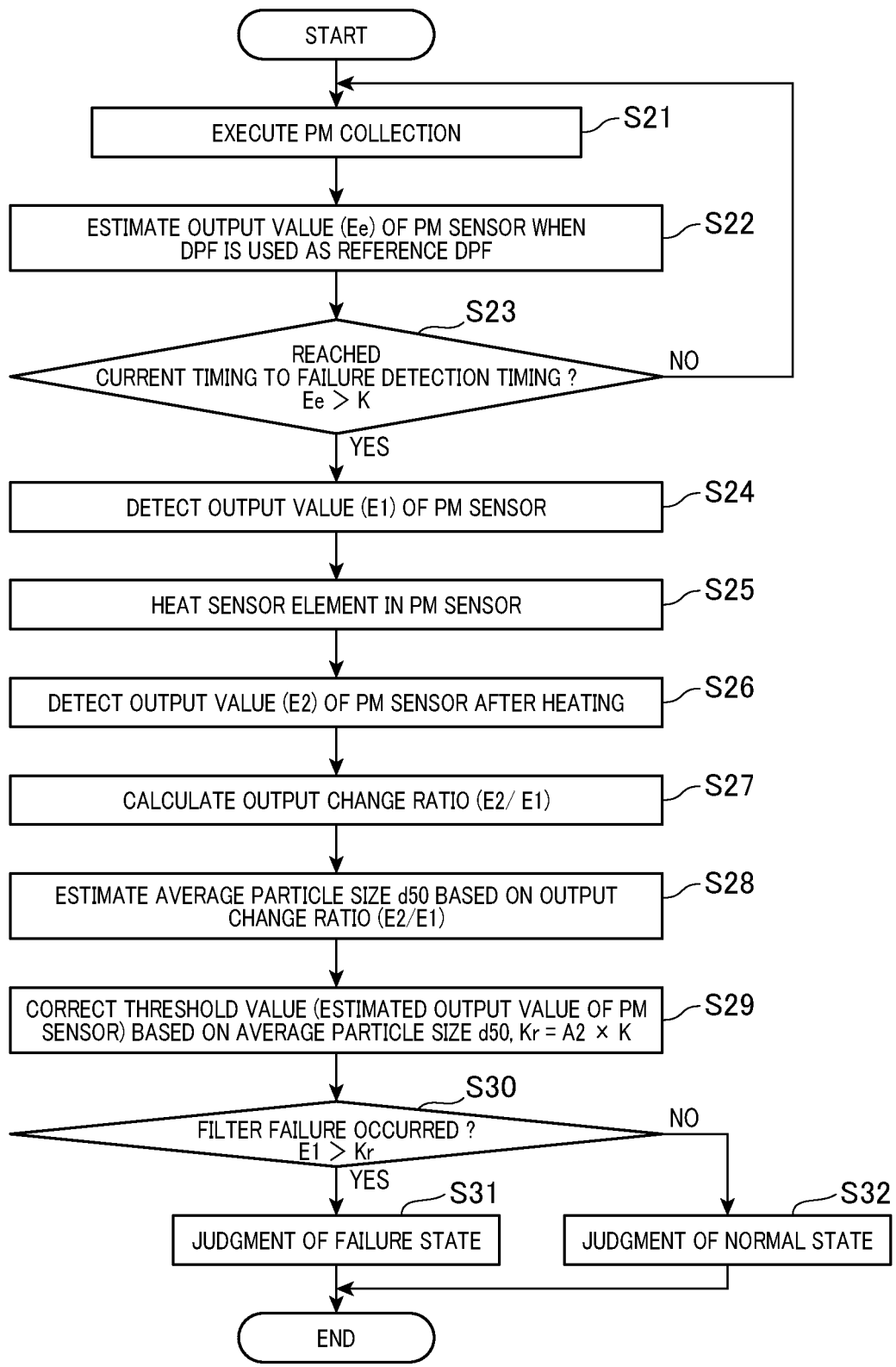
FIG. 10 is a view showing a flow chart of a failure detection process according to the second exemplary embodiment.

FIG. 10 is a view showing a flow chart of the failure detection process according to the second exemplary embodiment. The control unit 6 executes the processes shown in FIG. 10 instead of using the processes shown in FIG. 6. The processes in step S29 and S30 shown in FIG. 10 are different from the processes in step S9 and S10 according to the first exemplary embodiment shown in FIG. 6. Other processes in step S21 to S28, S31 and S32 shown in FIG. 10 are the same as the processes in step S1 to S8, S11 and S12 according to the first exemplary embodiment shown in FIG. 6.

Figure 11:
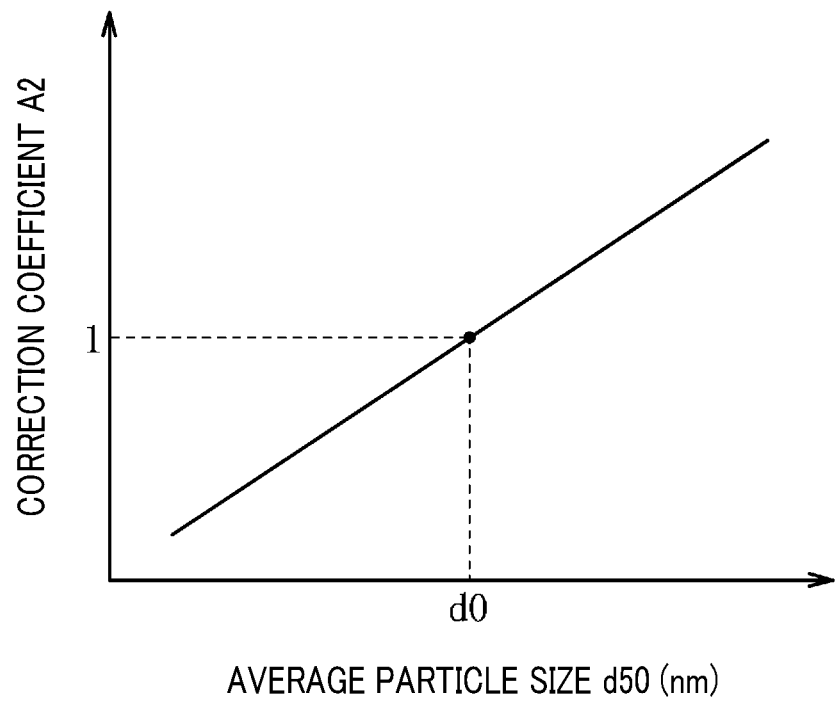
FIG. 11 is a view showing a relationship between an average particle size of PM and a correction coefficient of a threshold value.

In the process shown in FIG. 10, the threshold value K to be used by the failure detection (the predetermined value K shown in FIG. 4, as the estimated output value Ee at the failure detection timing) is corrected (step S29) on the basis of the average particle size d50 estimated in step S28. Specifically, as shown in FIG. 11, the relationship (map) between the average particle size d50 and the correction coefficient A2 as the threshold value is stored in the memory 61 in advance. In the relationship shown in FIG. 11, the smaller the average particle size d50, the smaller the correction coefficient A2. Although FIG. 11 shows the proportional relationship between the average particle size d50 and the correction coefficient A2, it is acceptable to have a relationship between them, designated by using a convex curve upward or a concave curve downward.

In addition, the correction coefficient A2 has a value of 1 when the average particle size d50 has the predetermined reference value d0 (for example, 60 nm), the correction coefficient A2 has a value of less than 1 when the average particle size d50 is smaller than the predetermined reference value d0, and the correction coefficient A2 has a value of more than 1 when the average particle size d50 is larger than the predetermined reference value d0. In other words, it is determined to have the correction coefficient A2 so that the corrected threshold value obtained in step S29 becomes the threshold value when the average particle size d50 has the predetermined reference value d0.

The control unit 6 calculates the correction coefficient A2 on the basis of the relationship shown in FIG. 11 and the average particle size d50 of PM estimated in step S28. The control unit 6 calculates the corrected threshold value Kr by multiplying the threshold value L and the correction coefficient A2 together. That is, the control unit 6 executes the calculation of Kr=A2×K. This calculation makes it possible to correct the threshold value so that the amount of PM is reduced according to the reducing of the average particle size d50, i.e. the threshold value is reduced. In other words, this makes it possible to correct the threshold value in the same direction in which the output of the PM sensor 5 varies due to the average particle size d50. For example, when the output value of the PM sensor 5 is a small value due to the reduction of the average particle size d50, the threshold value is reduced.

Next, the control unit 6 detects whether the output value E1 detected in step S24 is larger than the corrected threshold value Kr (step S30).

When the detection result indicates that the output value E1 is larger than the corrected threshold value Kr ("YES" in step S30), it is detected that the DPF 4 is in a failure (step S31). On the other hand, when the detection result indicates that the output value E1 is not more than the corrected threshold value Kr ("NO" in step S30), it is detected that the DPF 4 works correctly (is in a normal state).

As previously explained, similar to the effects of the first exemplary embodiment, the second exemplary embodiment has the same effects to suppress the failure detection results from varying due to the average particle size because of using the corrected threshold value instead of using the corrected output value of the PM sensor 5, Third Exemplary Embodiment Next, a description will be given of the failure detection process according to the third exemplary embodiment of the present invention.

Hereinafter, a difference between the third exemplary embodiment and the first exemplary embodiment will be mainly explained. In the third exemplary embodiment, the control unit 6 executes the failure detection process which is different in process from that of the first exemplary embodiment. Other processes of the third exemplary embodiment are the same as those in the first exemplary embodiment previously described. A description will now be given of the failure detection process according to the third exemplary embodiment.

In the failure detection process shown in FIG. 6, the control unit 6 estimates the output value Ee of the PM sensor 5 when the DPF 4 is used as the reference DPF (step S2). The control unit 6 detects whether the failure detection timing has been reached on the basis of the detection result whether the estimated output value Ee has reached the predetermined value K (step S3).

Figure 12:
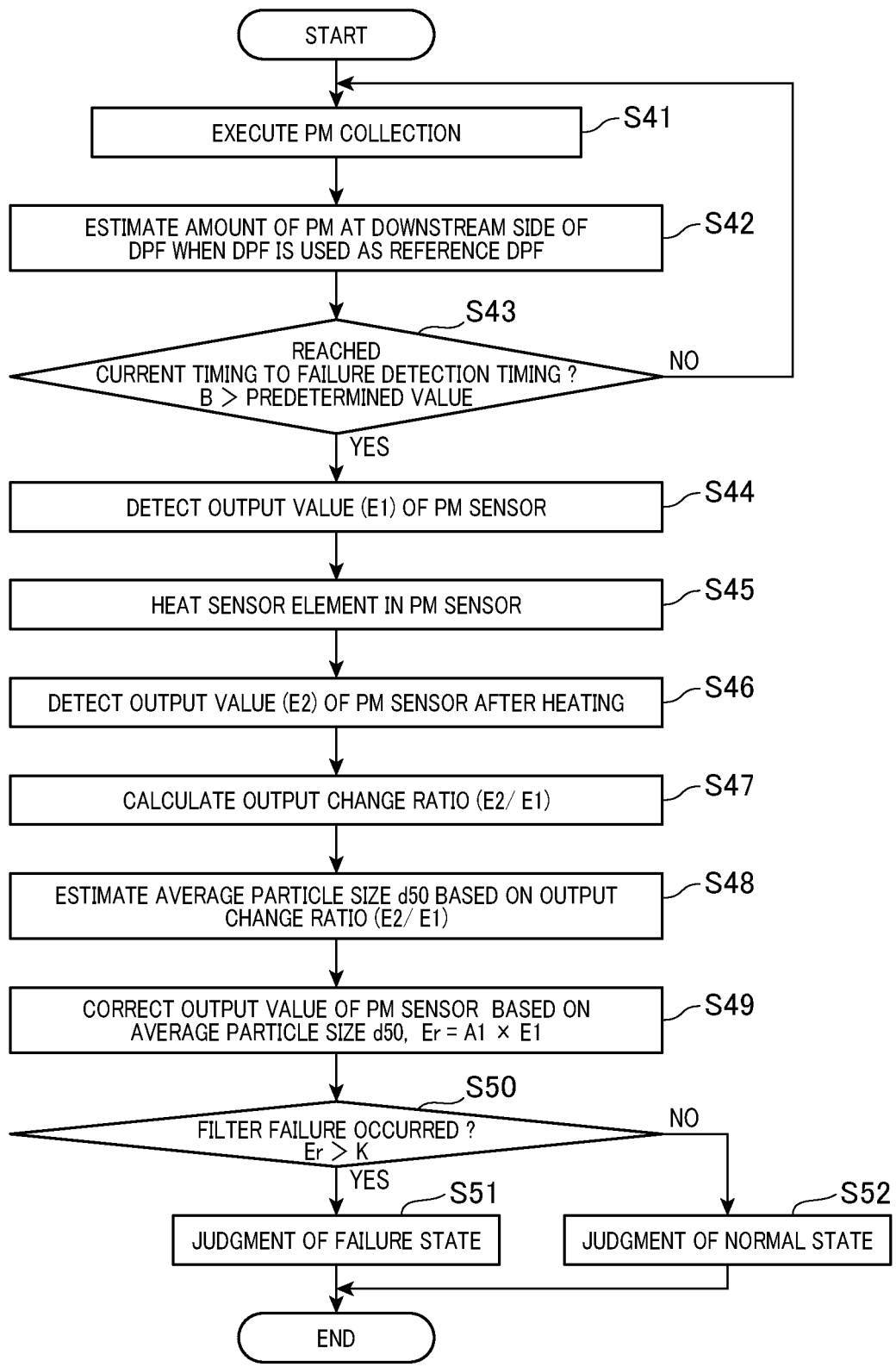
FIG. 12 is a view showing a flow chart of a failure detection process according to a third exemplary embodiment.

On the other hand, the control unit 6 according to the third exemplary embodiment executes the process shown in FIG. 12, instead of executing the process shown in FIG. 6. That is, the processes in step S42 and S43 are different from those in step S2 and S3 shown in FIG. 6. Other processes (i.e. the processes in step S41, S44 to S52 shown in FIG. 12) are the same as those in step S1, S4 to S12 shown in FIG. 6.

As shown in FIG. 12, the control unit 6 starts to execute the electrostatic collection process in step S41, estimates the amount f of PM at each timing (per unit timing) which passes through the DPF 4 on the operation state of the engine 2 when the DPF 4 is used as the reference DPF, and estimates the accumulation amount B of the estimated PM amount f at each timing (step S42).

The method of estimating the accumulation amount B is the same as the method of estimating the accumulation amount B which is obtained to calculate the estimated output value Ee in the process in step S2 shown in FIG. 6. As previously described, in step S42, the control unit 6 does not obtain the estimated output value E2, but estimates the accumulation amount B, which correlates with the estimated output value Ee, before the estimated output value Ee is calculated.

Next, the control unit 6 detects whether the current timing has reached the failure detection timing (step S43) on the basis of the detection result which represents whether the accumulation amount B which has been estimated in step S42 exceeds the predetermined value. This predetermined value has the predetermined value K (the threshold value K in step S50) shown in FIG. 4 as the converted value of the output value of the PM sensor 5.

When the detection result indicates that the accumulation amount B is less than the predetermined value ("NO" in step S43), the operation flow returns to step S41 because the current timing does not reach the failure detection timing.

On the other hand, when the detection result indicates that the accumulation amount B exceeds the predetermined value ("YES" in step S43), the operation flow progresses to step S44 and executes the processes following step S44 because the current timing has reached the failure detection timing.

The processes shown in FIG. 12 provide the same effects of the processes according to the exemplary embodiments previously described. It is acceptable for the control unit 6 to replace the processes in step S22 and S23 shown in FIG. 12 with the processes in step S42 and step S43 shown in FIG. 12.

Instead of executing the process in step S42 and step S43 shown in FIG. 12, it is further acceptable for the control unit 6 to estimate the amount of PM which has been collected by the Pm sensor 5 when the DPF 4 is used as the reference DPF, and detect whether the current timing has reached the failure detection timing on the basis of the result whether the estimated amount of PM exceeds the predetermined amount of PM. It is sufficient to estimate the predetermined amount of PM on the basis of the accumulation amount B of PM. These processes provide the same effects provided by the exemplary embodiments previously described.

Fourth Exemplary Embodiment

Next, a description will be given of the failure detection process according to the fourth exemplary embodiment of the present invention.

Hereinafter, a difference between the fourth exemplary embodiment and the previous exemplary embodiments will be mainly explained. In the fourth exemplary embodiment, the control unit 6 executes the failure detection process which is different in process details from that of the previous exemplary embodiments. Other processes of the fourth exemplary embodiment are the same as those in the exemplary embodiments previously described. A description will now be given of the failure detection process according to the fourth exemplary embodiment.

PM contains soot components (soot), soluble organic fraction (SOF) and sulfate component. SOF is composed of unburned fuel and lubricant or impregnated with soot. Sulfate is mist or drops made of oxidized material (sulfide) solved in water contained exhaust gas.

An amount of SOF in PM contained in exhaust gas varies due to the operation condition of the engine 2. Because SOF has a conductivity which is lower than that of soot, a resistance of PM varies due to the content of SOF in PM contained in exhaust gas. Accordingly, the output value of the PM sensor 5 varies due to the amount of SOF even if the PM sensor 5 collects the same average particle size and the same amount of PM. The fourth exemplary embodiment calculates the average particle size of PM while eliminating influence of SOF contained in PM.

A description will now be given of the failure detection process of estimating the average particle size of PM without the influence of SOF with reference to FIG. 13 to FIG. 16.

Figure 13:
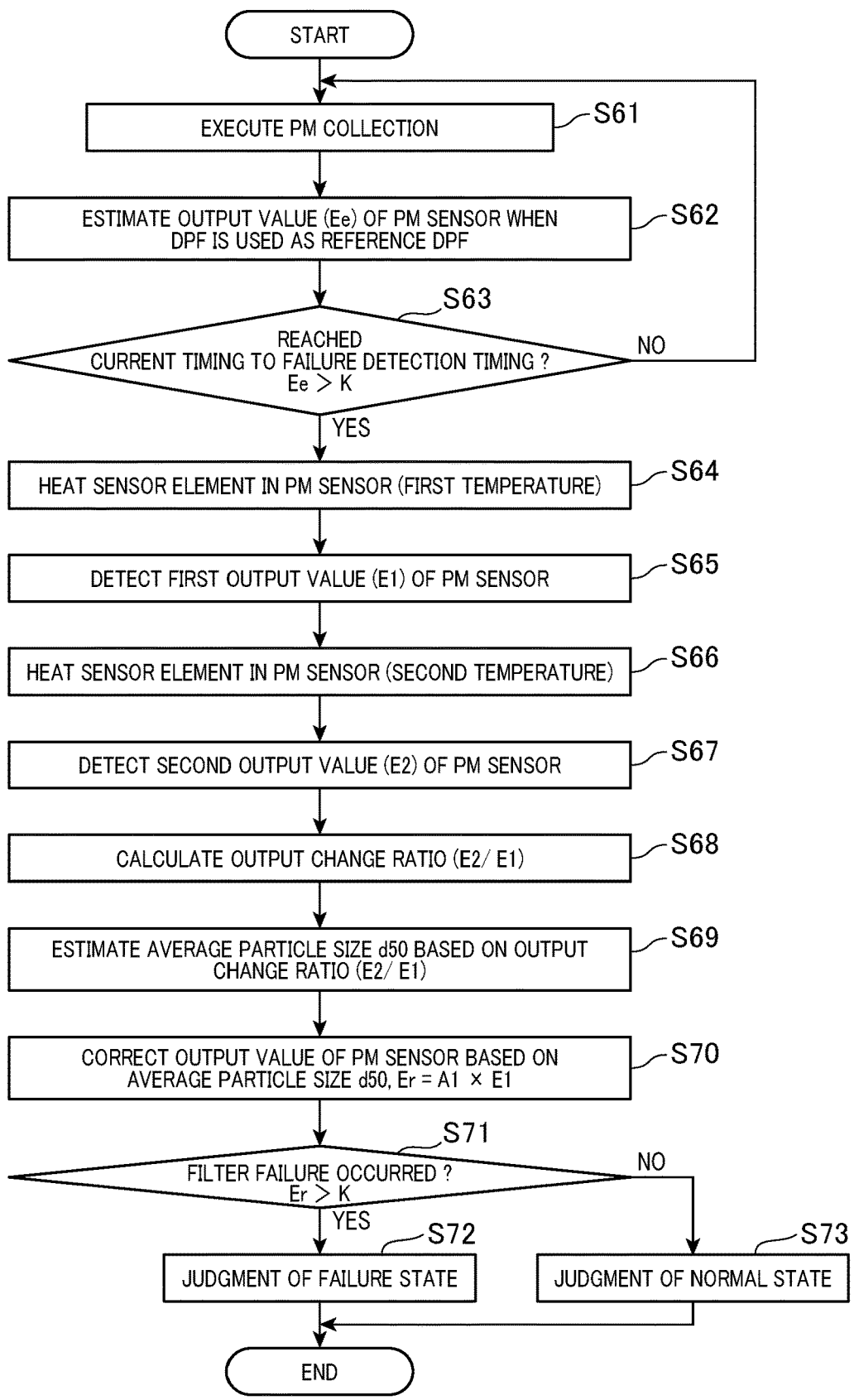
FIG. 13 is a view showing a flow chart of a failure detection process according to a fourth exemplary embodiment.

In the fourth exemplary embodiment, the control unit 6 executes the processes shown in FIG. 13, instead of executing the processes shown in FIG. 6. The PM sensor 5 does not collect any PM at the start timing when the control unit 6 starts to execute the processes shown in FIG. 13 are executed.

When the processes shown in FIG. 13 are started, the control unit 6 executes the electrostatic collection process (step S61), like the processes in step S1 to step S3 shown in FIG. 6, and estimates the output value Ee of the PM sensor 5 when the DPF 4 is used as the reference DPF (step S62), and detects whether the output value Ee of the PM sensor 5 exceeds the predetermined value K (step S63).

When the detection result indicates that the output value Ee of the PM sensor 5 is less than the predetermined value K ("NO" in step S63), the operation flow returns to step S61 because the current timing does not reach the failure detection timing, and the control unit 6 continues the estimation processes of executing the electrostatic collection and estimating the output value Ee of the PM sensor 5 (step S61, step S62).

On the other hand, when the detection result indicates that the output value Ee of the PM sensor 5 exceeds the predetermined value K ("YES" in step S63), the control unit 6 determines that the current timing has reached the failure detection timing, and executes the processes in step S64 to step S69 to estimate the average particle size d50 (median diameter) of PM contained in exhaust gas. Specifically, as shown in the upper half part of FIG. 14 which indicates the change of a temperature of the sensor element 52 which corresponds to the elapse of time counted from the start timing when the PM sensor 5 collects PM), the heater 54 generates heat energy to heat the sensor element 52 at a first temperature at which SOF is evaporated, but no soot is burned (step S64).

Figure 15:
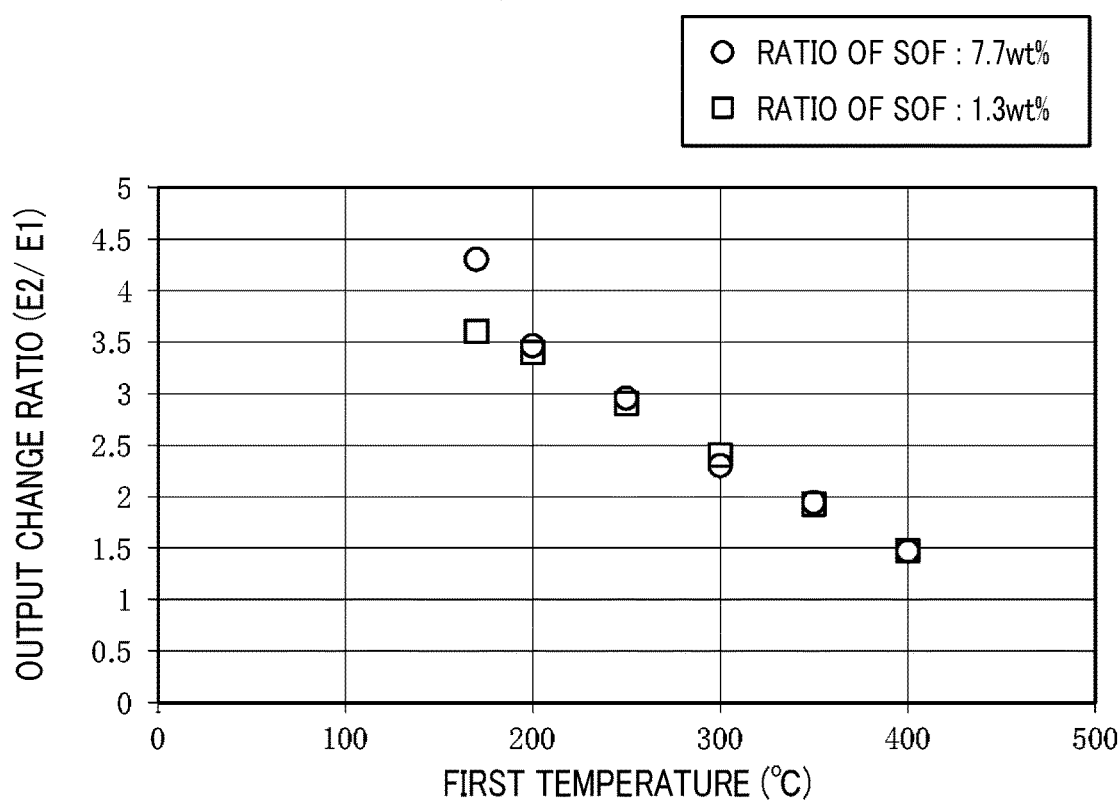
FIG. 15 is a view showing a change rate of the output of the PM sensor due to a first temperature when an average particle size of PM is constant.

FIG. 15 is a view showing an optimum range of the first temperature. In more detail, FIG. 15 shows the output change ratio (E2/E1) of the PM sensor 5 to the first temperature when the average particle size (approximately 55 nm) of PM is constant. The vertical axis in FIG. 15 indicates the output change ratio (E2/E1) represents the change ratio of the second output value E2 to the first output value E1, where the first output value E1 is the output value of the PM sensor 5 when the sensor element 52 is heated at the first temperature, and the second output value E2 is the output value of the PM sensor 5 at the second temperature to burn soot. In FIG. 15, reference character "O" indicates the results obtained under the condition in which the engine rotation speed is 1,654 rpm, the torque is 24 Nm, the SOF ratio (weight percent concentration) in PM is 7.7 wt %, and reference character "□" designates the results obtained under the condition in which the engine rotation speed is 2,117 rpm, the torque is 83 Nm, the SOF ratio in PM is 1.3 wt %.

As shown in FIG. 15, during the temperature range of 200° C. to 400° C., the output change ratio (indicated by reference character "O") when the SOF ratio is large, and the output change ratio (indicated by reference character "□") when the SOF ratio is smaller have approximately the same values. On the other hand, when the first temperature is less than 200° C., the output change ratio (indicated by reference character "O") when the SOF ratio is large becomes greater than the output change ratio (indicated by reference character "□") when the SOF ratio is small. This means that the output value E1 of the PM sensor 5 varies at the first temperature due to the SOF ratio because SOF is not sufficiently evaporated at the first temperature of less than 200° C. Specifically, the larger the SOF ratio, the larger the resistance of PM, as a result, the output value E1 of the PM sensor 5 becomes reduces. On the other hand, because SOF is evaporated at the second temperature, the output value E2 of the PM sensor 5 becomes constant at the second temperature regardless of the SOF ratio. This makes it possible to estimate that the output change ratio E2/E1 increases according to increasing of the SOF ratio when the first temperature is less than 200° C.

As previously described, it is difficult to avoid influence of SOF to the output charge ratio when the first temperature is less than 200° C. In other words, the output charge ratio varies due to the SOF ratio when the first temperature is less than 200° C.

On the other hand, not shown in FIG. 15, the inventors of the present invention have found that the output value of the PM sensor 5 is gradually reduced at the first temperature of more than 400° C. This means that soot is burned when the first temperature exceeds 400° C.

Accordingly, it is preferable for the first temperature to be not less than 200° C. and not more than 400° C.

Figure 14:
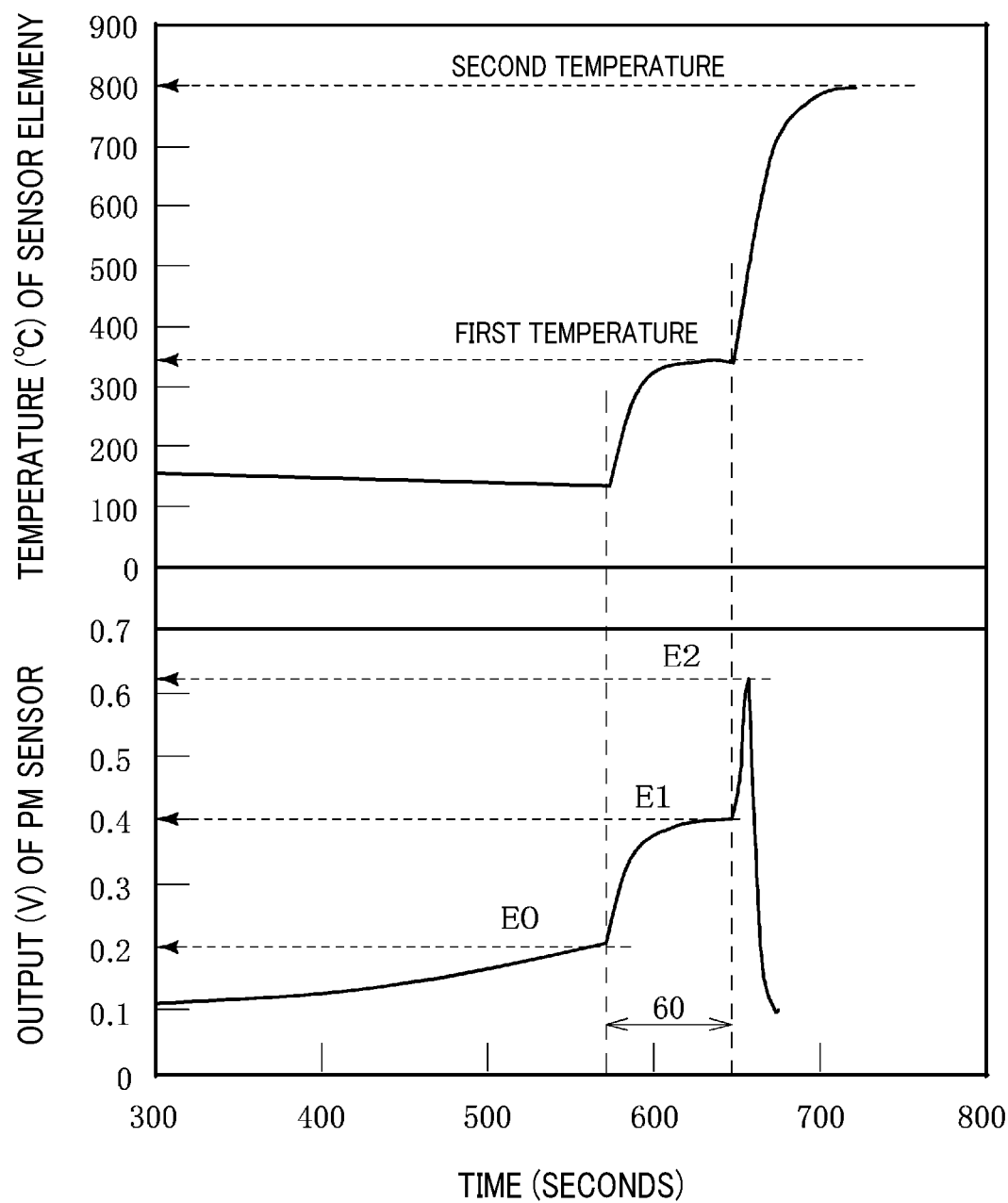
FIG. 14 is a view, in which an upper half part shows a change of a temperature of the sensor element corresponding to an elapsed period of time counted from a start of collecting PM element temperature, and a lower half part shows a variation of the output of the PM sensor, which show a heating control of the sensor element used in fourth to eleventh exemplary embodiments, and shows a variation of the output of the PM sensor due to the heating control.

In step S64, the output of the PM sensor 5 increases when the sensor element 52 is heated at the first temperature, as shown in the bottom half part in FIG. 14 (which shows the change of the output of the PM sensor 5 in the elapse of tome counted from the start timing of the PM collection by the PM sensor 5). This means that the crystal structure of PM changes when the sensor element 52 is heated and PM collected by the sensor element 52 is also heated, such that the conductivity of Pm improves, in other words, the resistivity of PM reduces. FIG. 14 shows an example when the first temperature is 350° C.

In step S64, it is preferable to have the first temperature heating period of 30 seconds to maintain the sensor element 52 at the first temperature. If the first temperature heating period is less than 30 seconds, it is difficult to have a stable state to maintain the sensor element 52 at the first temperature, and there is a possible insufficient evaporation of SOF.

It is acceptable to have the first temperature heating period of less than 30 seconds to heat the sensor element 52 if SOF can be adequately evaporated in this period.

Further, it is acceptable to have a long heating period, but this heating period needs a long detection period. Accordingly, it is preferable to use the first temperature heating period of not more than three minutes. FIG. 14 shows an example having the first temperature heating period of 60 seconds.

As previously described, it is possible to eliminate the influence of SOF to the output of the PM sensor 5 by heating the sensor element 52 at the first temperature. In addition, because PM has a different temperature when a temperature of the exhaust gas varies due to the operation state of the engine 2, the output of the PM sensor 5 varies by the temperature characteristics of the resistance of PM. However, the heating process in step S64 heats the sensor element 52 to maintain a temperature of PM collected on the sensor element 52 constant, this makes it possible to avoid the output of the PM sensor 5 from being influenced by the temperature of exhaust gas.

After the process in step S64, the control unit 6 detects the first output value E1 of the PM sensor 5 (step S65). At this time, the control unit 6 detects, as the first output value E1, the peak value of the output of the PM sensor 5 during the first temperature heating period in which the sensor element 52 is maintained at the first temperature.

Next, as shown at the upper half part in FIG. 14, the control unit 6 instructs the heater 54 to heats the sensor element 52 at the second temperature in which soot is burned (step S66) after heating of the sensor element 52 at the first temperature. It is preferable to have the second temperature to be not less than 600° C. and not more than 100° C. When the second temperature is less than 600° C., soot cannot be completely burned. When the second temperature exceeds 1000° C., there is a possible case in which the sensor element 52 and the opposing electrodes 53 are damaged at a high temperature. FIG. 14 shows an example when the second temperature is 800° C.

It is preferable to have a second temperature heating period of not less than 30 seconds to heat and maintain the sensor element 52 at the second temperature. If the second temperature heating period is less than 30 seconds, the heating temperature is fluctuated, and it is accordingly difficult to adequately burn soot. Further, this causes a possible case in which it is difficult for the control unit 6 to correctly detect the peak value E2 of the output of the PM sensor 5 in step S67 which will be explained later. If it is possible to correctly detect the peak value E2 of the output of the PM sensor 5, it is sufficient to use the second temperature heating period of less than 30 seconds. It is acceptable to have a long heating period as the second temperature heating period, but this heating period needs a long detection period. Accordingly, it is preferable to use a second temperature heating period of not more than three minutes.

As shown in the bottom half part in FIG. 14, the output of the PM sensor 5 increases from the first output value E1 by heating the sensor element 52 at the second temperature. Specifically, the output of the PM sensor 5 firstly increases to the peak value E2 according to the elapse of time counted from the start timing of the second temperature heating period. After the peak value E2 of the output of the PM sensor 5, the output of the PM sensor 5 reduces because soot is completely burned. This phenomenon means that no soot is burned during the period of the start timing of the second temperature heating period to the timing at which the output of the PM sensor 5 reaches the peak value E2. The output of the PM sensor 5 further increases from the first output value E1 during the period from the start timing to heat the sensor element 52 at the second temperature to the timing at which the output of the PM sensor 5 reaches the peak value E2. This further promotes the conversion of the crystal structure of PM collected in the sensor element 52 to a graphite state. The graphite structure of PM has a high conductivity by heating the sensor element 52 at the second temperature which is higher than the first temperature.

Next, the control unit 6 detects, as the second output value E2, the peak value of the output of the PM sensor 5 (step S67) which has increased by heating the sensor element 52 at the second temperature. Specifically, for example, it is acceptable for the control unit 6 to monitor the output of the PM sensor 5 from the heating start timing so as to detect the peak value E2 of the output of the PM sensor 5. It is also acceptable to detect a period of time in advance, at which the output of the PM sensor 5 has a peak value, and uses, as the peak value, the output of the PM sensor 5 at the detected period of time.

Next, the control unit 6 calculates the output change ratio E2/E1 (step S68) between the output value E1 and the output value E2 of the PM sensor 5 detected in step S65 and step S67. The output change ratio E2/E1 is a change ratio of the second output value E2 to the first output value E1. Next, the control unit 6 estimates the average particle size d50 of PM contained in exhaust gas (step S69) on the basis of the output change ratio E2/E1 calculated in step S68.

Figure 16:
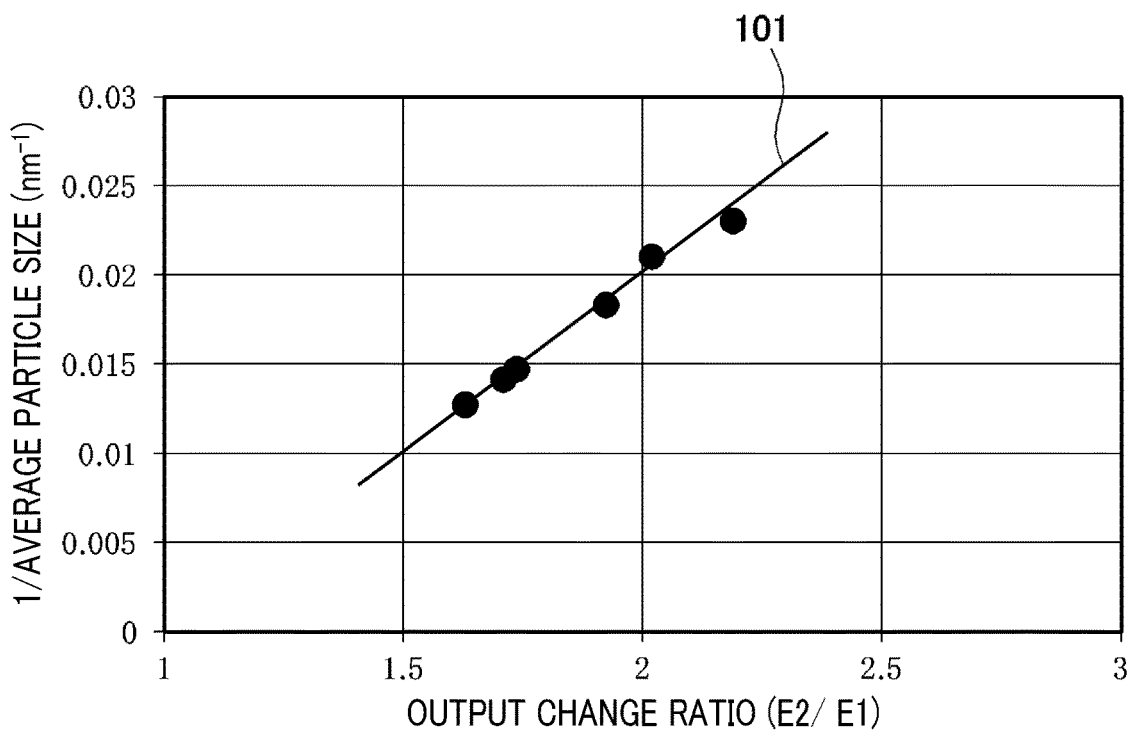
FIG. 16 is a view showing a relationship between an output change ratio E2/E1 and the average particle size of PM, wherein E1 represents an output value of the PM sensor at a first temperature at which SOF is evaporated and no soot is burned, and E2 represents an output value of the PM sensor at a second temperature in which soot is burned.

FIG. 16 shows a relationship between the output change ratio E2/E1 and the average particle size d50 of PM, where the output change ratio E2/E1 is the change ratio of the first output value E1 to the second output value E2.

In FIG. 16, the vertical axis indicates a reverse value of the average particle size d50, and each point represents an experimental result by using the engine Exhaust Particle Sizer (EEPS) Spectrometer previously described.

As shown in FIG. 16, the output change ratio E2/E1 correlates with the average particle size d50 of PM, where the output change ratio E2/E1 is a change ratio of the second output value E2 at the second temperature to the first output value E1 at the first temperature. Specifically, the output change ratio E2/E1 and the average particle size d50 have approximately a positive correlation (a proportional relationship). The relationship 101 shown in FIG. 16 has been detected and stored in the memory 61 in advance.

As shown in FIG. 15, even if the average particle size of PM is constant, the output change ratio E2/E1 varies due to the change of the first temperature. Accordingly, it is necessary that the first temperature when the relationship 101 shown in FIG. 16 is detected is equal to the first temperature used in step S64.

In step S69, the control unit 6 estimates the average particle size d50 on the basis of the relationship 101 shown in FIG. 16 and the output change ratio E2/E1 currently calculated in step S68. The average particle size d50 calculated in step S69 represents the average particle size of PM which has been discharged to the downstream of the DPF 4 during the period counted from the start of the electrostatic collection in step S61 to the timing when the current timing reaches the failure detection timing.

Next, similar to the process in step S9 shown in FIG. 6, the control unit 6 corrects the first output value E1 detected in step S65 on the basis of the average particle size d50 which has been estimated in step S69. Specifically, the control unit 6 obtains the correction coefficient A1, which corresponds to the average particle size d50, from the map shown in FIG. 9. The control unit 6 obtains the corrected output value Er of the PM sensor 5 by multiplying the first output value E1 and the correction coefficient A1 together. That is, the control unit 6 executes the calculation of Er=A1×E1.

Next, similar to the processes in step S10 to step S12 shown in FIG. 6, the control unit 6 detects whether the corrected output value Er of the PM sensor 5 is greater than the predetermined value K (step S71). When the detection result indicates that the corrected output value Er of the PM sensor 5 is greater than, i.e. more than the predetermined value K ("YES" in step S71), the control unit 6 judges that the DPF 4 is has failed (step S72). On the other hand, when the detection result indicates that the corrected output value Er of the PM sensor 5 is not more than the predetermined value K ("NO" in step S71), the control unit 6 judges that the DPF 4 is working correctly (is in a normal state) (step S73). After the process in step S72 or step S73, the control unit 6 finishes the processes indicated by the flow chart shown in FIG. 13.

In the first to third exemplary embodiments previously described, the control unit 6 estimates the average particle size pf Pm on the basis of the output change ratio E2/E0, where the output value E0 is an output value of the PM sensor 5 at the timing when the sensor element 52 is heated at the first temperature, and the output value E2 is an output value of the PM sensor 5 at the timing when the sensor element 52 is heated at the second temperature.

On the other hand, the control unit according to the fourth exemplary embodiment estimates the average particle size on the basis of the output change ratio E2/E1 which is obtained by using the output value E1 of the PM sensor 5 as a reference value when the sensor element 52 is heated at the first temperature at which SOF is evaporated, but no soot is burned. This makes it possible to obtain the average particle size of PM with high accuracy from which the influence due to SOF and a temperature of exhaust gas is eliminated. This makes it possible to suppress the output of the PM sensor 5 from varying due to variation of the average particle size, and further suppress the output of the PM sensor 5 from varying due to a content of SOF contained in PM, and the operation condition (a temperature of exhaust gas) of the engine 2. As a result, this makes it possible to have the effects, for example, to suppress an incorrect failure detection of the PM sensor 5 from occurring, in which the DPF is detected as having failed in spite of the fact in which the DPF is working correctly, or the DPF is detected as working correctly in spite of the fact in which the DPF has failed.

Because the control unit 6 according to the fourth exemplary embodiment corrects the output E1 of the PM sensor 5 at the first temperature from which the influence due to SOF and a temperature of exhaust gas has been eliminated, and executes the DPF failure detection on the basis of the corrected output value Er of the PM sensor 5, this makes it possible to more eliminate the execution of the DPF failure detection process form being influenced by SOF and a temperature of exhaust gas.

Fifth Exemplary Embodiment

Next, a description will be given of the failure detection process according to the fifth exemplary embodiment of the present invention.

Hereinafter, a difference between the fifth exemplary embodiment and the previous exemplary embodiments will be mainly explained. In the fifth exemplary embodiment, the control unit 6 executes the failure detection process which is different in process from that of the fourth exemplary embodiment. Other processes of the fifth exemplary embodiment are the same as the processes in the fourth exemplary embodiment previously described. A description will now be given of the failure detection process according to the fifth exemplary embodiment.

Figure 17:
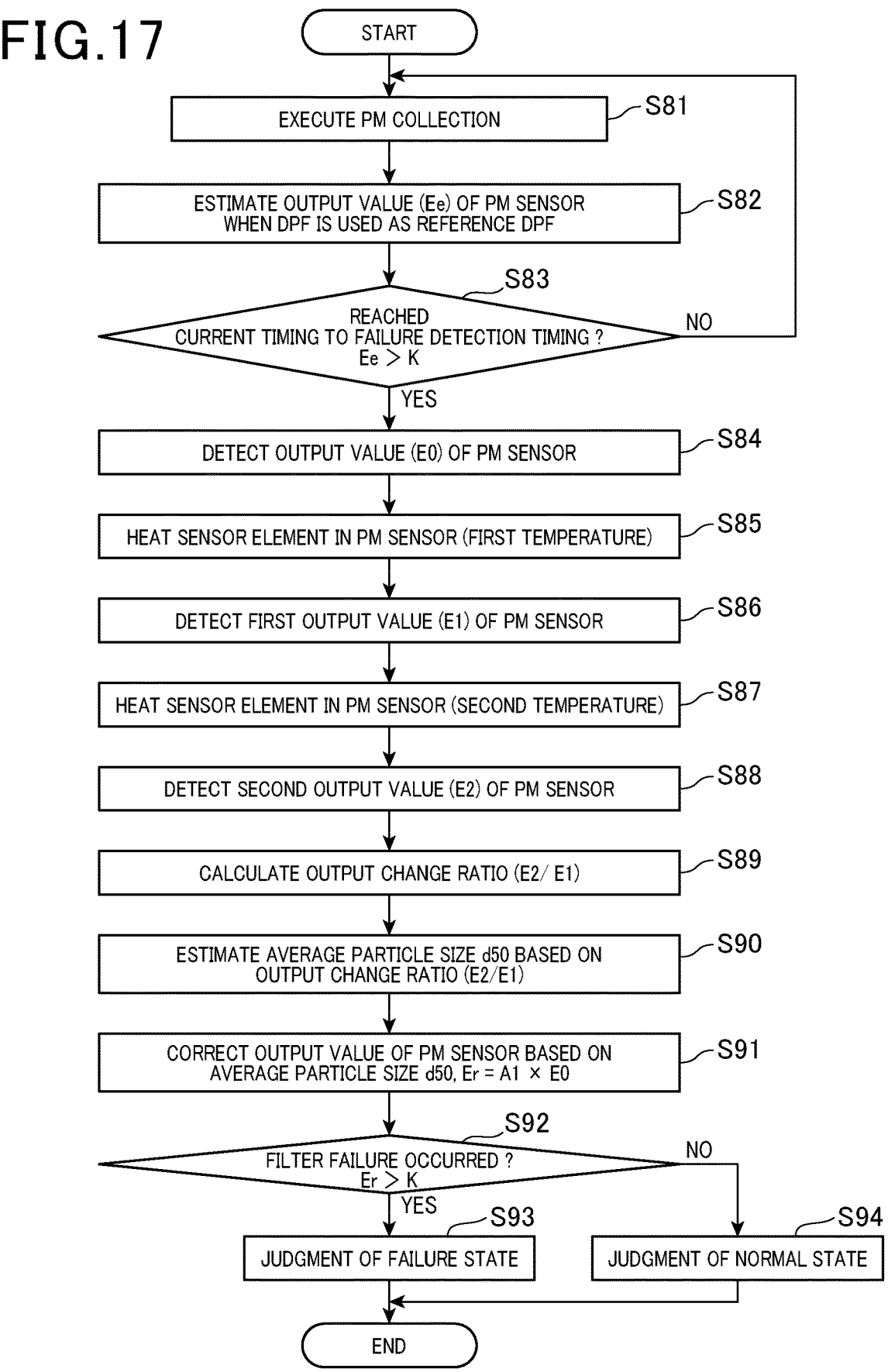
FIG. 17 is a view showing a flow chart of a failure detection process according to a fifth exemplary embodiment.

The control unit 6 executes the failure detection process shown in FIG. 17. The processes in step S84 and step S91 shown in FIG. 17 are different from the processes shown FIG. 13. Other processes (the processes in step S81 to step S83, step S85 to step S90, step S92 to step S94) shown in FIG. 17 are the same as the processes in step S61 to step S69, step S71 to step S73 shown in FIG. 13.

When starting the processes in the flow chart shown in FIG. 17, the control unit 6 executes the electrostatic collection process (step S81), similar to the processes in step S61 to step S63 shown in FIG. 13. The control unit 6 estimates the output value Ee of the OM sensor 5 (step S82) when the DPF 4 is used as the reference DPF, and detects whether the output value Ee of the PM sensor 5 exceeds the predetermined value K (step S83).

When the detection result indicates that the output value Ee of the PM sensor 5 is less than the predetermined value K ("NO" in step S83), the control unit 6 judges that the current timing has not yet reached the failure detection timing, and the operation flow returns to step S81 so as to continue the execution of the electrostatic collection process and the estimation of the output value Ee of the PM sensor 5 (step S81 and step S82).

On the other hand, when the detection result indicates that the output value Ee of the PM sensor 5 exceeds the predetermined value K ("YES" in step S83), the control unit 6 detects the output value E0 of the PM sensor 5 (step S84) before the sensor element 52 is heated to the first temperature in step S85. As shown in the bottom half part in FIG. 14, the output value E0 of the PM sensor 5 is the output of the PM sensor 5 at the start timing to heat the sensor element 52 to the first temperature.

Next, similar to the processes in step S64 to step S69 shown in FIG. 13, the control unit 6 estimates the average particle size d50 of PM (step S85 to step S90) on the basis of the output change ratio E2/E1, wherein the output value E1 represents an output value of the PM sensor at the first temperature at which SOF is evaporated, but soot does not burn, and the output value E2 represents an output value of the PM sensor 5 at the second temperature at which soot is burned.

Next, the control unit 6 corrects the output value E0 of the PM sensor 5 (step S90), which has been detected in step S84. Specifically, similar to the process in step S9 shown in FIG. 6, the control unit 6 obtains the correction coefficient A1, which corresponds to the average particle size d50, from the map shown in FIG. 9. The control unit 6 calculates the corrected output value Re of the PM sensor 5 by multiplying the output value E0 of the PM sensor 5 and the correction coefficient A1 together. That is, the control unit 6 executes the calculation of Er=A1×E0.

Next, similar to the processes in step S71 to step S73 shown in FIG. 13, the control unit 6 detects whether the corrected output value Er of the PM sensor 5 is greater than the predetermined value K (step S92).

When the detection result indicates that the corrected output value Er of the PM sensor 5 is more than the predetermined value K ("YES" in step S92), the control unit 6 detects that the DPF has failed (step S93). On the other hand, when the detection result indicates that the corrected output value Er of the PM sensor 5 is not more than the predetermined value K ("NO" in step S92), the control unit 6 detects that the DPF 4 is working correctly (is in a normal state) (step S94). After the process in step S93 or step S94, the control unit finishes the processes shown in the flow chart of FIG. 17.

As previously described, the control unit 6 according to the fourth exemplary embodiment executes the correction of the output value E1 of the PM sensor 5 at the first temperature. On the other hand, the control unit 6 according to the fifth exemplary embodiment executes the correction of the output value E0 of the PM sensor 5 before heating the sensor element 15 at the first temperature (or at the start timing of the heating of the sensor element 52 to the first temperature). This makes it possible for the control unit 6 to execute the failure detection process of the DPF while eliminating the influence due to SOF.

Sixth Exemplary Embodiment

Next, a description will be given of the failure detection process according to the sixth exemplary embodiment of the present invention.

Hereinafter, a difference between the sixth exemplary embodiment and the exemplary embodiments previously described will be mainly explained. In the sixth exemplary embodiment, the control unit 6 executes the failure detection process which is different in process from that of the exemplary embodiments previously described. Other processes of the sixth exemplary embodiment are the same as the processes in each of the exemplary embodiments previously described. A description will now be given of the failure detection process according to the sixth exemplary embodiment.

Figure 18:
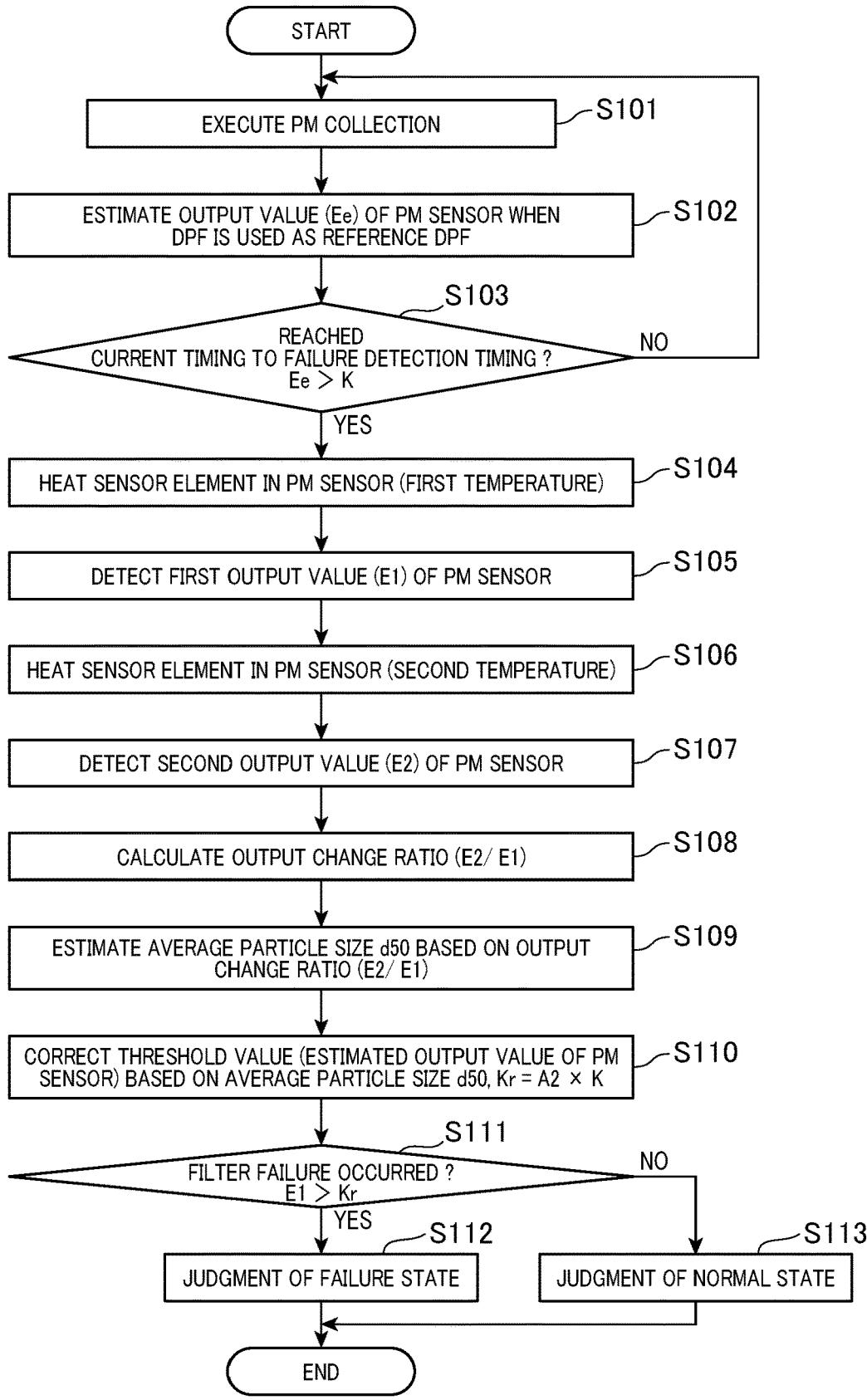
FIG. 18 is a view showing a flow chart of a failure detection process according to a sixth exemplary embodiment.

The control unit 6 executes, as the failure detection process, the processes in the flow chart shown in FIG. 18. The processes in step S110 and step S111 shown in FIG. 18 are different from the processes in step S70 and step S71 shown in FIG. 13. Other processes (step S110 to step S109, step S112, step S113) of the sixth exemplary embodiment are the same as the processes in step S61 to step S69, step S72 and step S73 shown in FIG. 13.

When starting to execute the processes in the flow chart shown in FIG. 18, the control unit 6 estimates the average particle size d50 of PM (step S101 to step S109) on the basis of the output change ratio E2/E1 when the current timing reaches the failure detection timing, similar to the processes in step S61 to step S69 shown in FIG. 13, wherein the output value E1 represents an output value of the PM sensor at the first temperature and the output value E2 represents an output value of the PM sensor 5 at the second temperature.

Next, in step S110 shown in FIG. 18, similar to the process in step S29 shown in FIG. 10, the control unit 6 corrects the threshold value K to be used in the failure detection process on the basis of the average particle size d50 of PM. Specifically, the control unit 6 obtains the correction coefficient A2, which corresponds to the average particle size d50, from the map shown in FIG. 11. The control unit 6 calculates the corrected threshold value Kr by multiplying the threshold value K and the correction coefficient A2 together. That is, the control unit 6 executes the calculation of Kr=A2×K.

Next, the control unit 6 detects whether the output value E1 of the PM sensor 5 at the first temperature detected in step S105 shown in FIG. 18 is more than the corrected threshold value Kr (step S111).

When the detection result indicates that the output value E1 of the PM sensor 5 is more than the corrected threshold value Kr ("YES" in step S111), the control unit 6 judges that the DPF 4 has failed (step S112). On the other hand, when the detection result indicates that the output value E1 of the PM sensor 5 is not more than the corrected threshold value Kr ("NO" in step S111), the control unit 6 judges that the DPF 4 is working correctly (is in a normal state) (step S113). After this process, the control unit 6 finishes the processes in the flow chart shown in FIG. 18.

As previously described, the control unit 6 executes the failure detection process according to the sixth exemplary embodiment in which the threshold value is corrected, like the failure detection process shown in the second exemplary embodiment, instead of correcting the output value of the Pm sensor 5. Similar to the failure detection process shown in the fourth and fifth exemplary embodiments, because the control unit 6 according to the sixth exemplary embodiment estimates the average particle size of PM on the basis of the output change ratio E2/E1 obtained on the basis of the output value E1 of the PM sensor 5 at the first temperature at which SOF is evaporated, but soot is not burned, it is possible to obtain the average particle size of PM while eliminating the influence due to SOF and a temperature of exhaust gas. Further, because the control unit 6 corrects the threshold value on the basis of the obtained average particle size of PM, and executes the failure detection process of the PDF on the basis of the comparison result between the corrected threshold value and the output value of the PM sensor 5, this makes it possible to suppress the detection results of the failure detection process from varying due to the average particle size of PM. In addition, it is possible to eliminate the influences due to SOF and operation conditions of the engine 2, (for example, exhaust gas).

Still further, because the control unit 6 according to the sixth exemplary embodiment executes the failure detection process of the DPF on the basis of the output value E1 of the PM sensor 5 from which the influence due to SOF and a temperature of exhaust gas have been eliminated, it is possible to execute the failure detection process correctly from which the influences due to SOP and a temperature of exhaust gas have further been eliminated.

Seventh Exemplary Embodiment

Next, a description will be given of the failure detection process according to the seventh exemplary embodiment of the present invention.

Hereinafter, a difference between the seventh exemplary embodiment and the exemplary embodiments previously described will be mainly explained. In the seventh exemplary embodiment, the control unit 6 executes the failure detection process which is different in process from that of the exemplary embodiments previously described. Other processes of the seventh exemplary embodiment are the same as the processes in each of the exemplary embodiments previously described. A description will now be given of the failure detection process according to the seventh exemplary embodiment.

Figure 19:
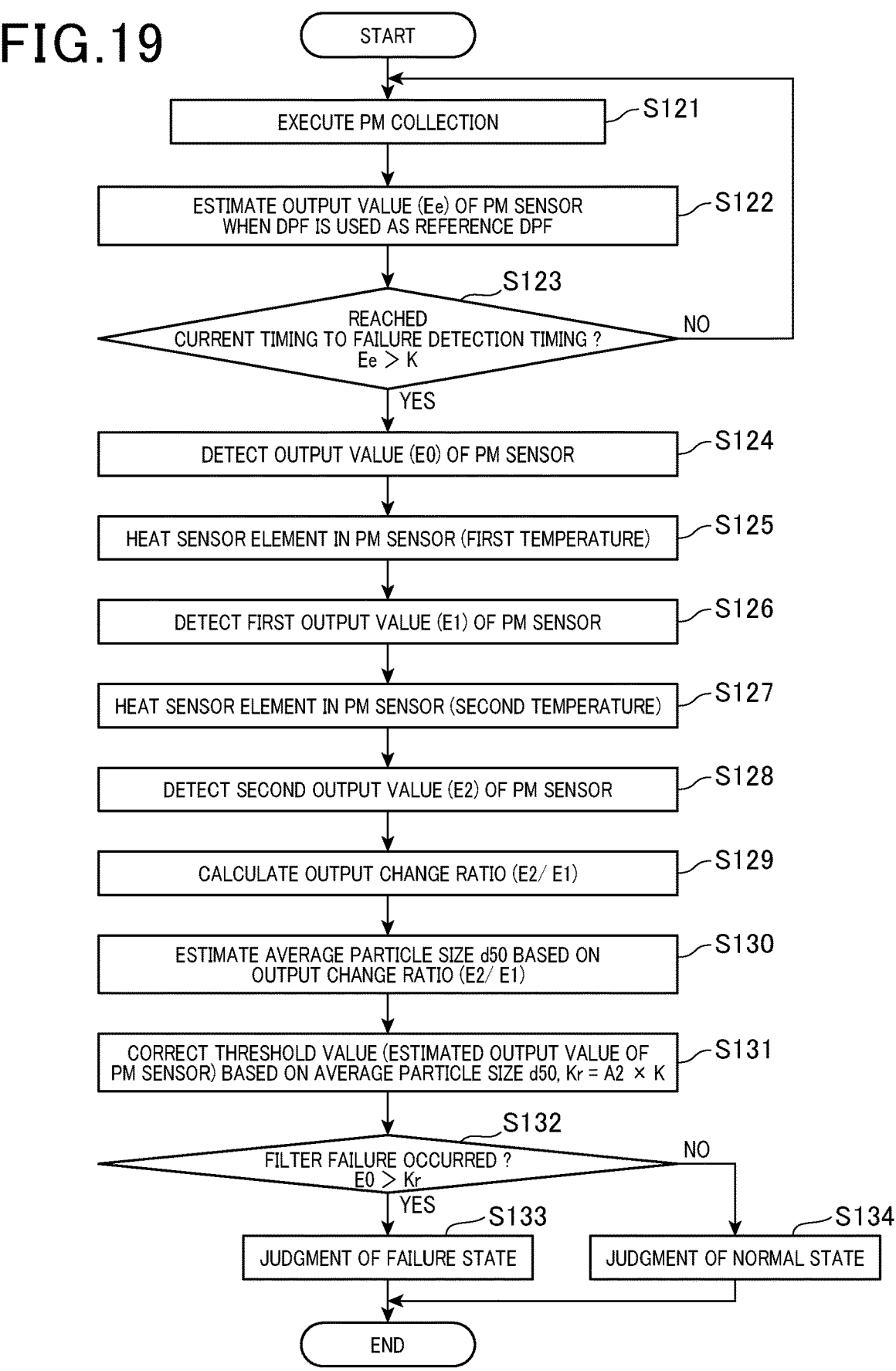
FIG. 19 is a view showing a flow chart of a failure detection process according to a seventh exemplary embodiment.

The control unit 6 executes the failure detection process shown in FIG. 19. In the flow chart shown in FIG. 19, a new process in step S124 is added into the processes in the flow chart shown in FIG. 18, and the process in step S111 shown in FIG. 18 is replaced with a new process in step S132. Other processes (in step S121 to step S123, step S125 to step S131, step S133, step S134) are the same as the processes in step S101 to step S110, step S112 and step S113 shown in FIG. 18.

When starting the execution of the processes in the flow chart shown in FIG. 19, the control unit 6 executes the electrostatic collection (step S121), like the processes in step S101 to step S102 shown in FIG. 18, estimates the output value Ee of the PM sensor 5 when the DPF 4 is used as the reference DPF (step S122), and detects whether the output value Ee of the PM sensor 5 exceeds the predetermined value K (step S123).

When the detection result indicates that the output value Ee of the PM sensor 5 is less than the predetermined value K ("NO" in step S123), the control unit 6 judges that the current timing does not reach the failure detection timing, and the operation flow returns to step S121. The control unit 6 continues the execution of the electrostatic collection of PM and the estimation of the output value Ee of the PM sensor 5 (step S121, S122).

On the other hand, when the output value Ee of the PM sensor 5 exceeds the predetermined value K ("YES" in step S123), the control unit 6 detects the output value E0 of the PM sensor 5 (step S124) before the sensor element 52 is heated (step S125). The output value E0 of the PM sensor 5 is the output of the PM sensor 5 at the timing for heating the sensor element 52 to the first temperature as shown in the bottom half part shown in FIG. 14.

Next, similar to the processes in step S104 to step S110 shown in FIG. 18, the control unit 6 estimates the average particle size d50 of PM on the basis of the output change ratio E2/E1, wherein the output value E1 represents an output value of the PM sensor 5 at the first temperature at which SOF is evaporated, but soot does not burn, and the output value E2 represents an output value of the PM sensor 5 at the second temperature at which soot is burned. The control unit 6 corrects the threshold value K on the basis of the average particle size d50 of PM (step S125 to step S131).

Next, the control unit 6 detects whether the output value E0 of the PM sensor 5 detected in step S124 is more than the corrected threshold value Kr (step S132).

When the detection result indicates that the output value E0 of the PM sensor 5 is more than the corrected threshold value Kr ("YES" in step S132), the control unit 6 judges that the DPF 4 has failed (step S133). On the other hand, when the detection result indicates that the output value E0 of the PM sensor 5 is not more than the corrected threshold value Kr ("NO" in step S132), the control unit 6 judges that the DPF 4 is working correctly (is in a normal state) (step S134). After this process, the control unit 6 finishes the processes in the flow chart shown in FIG. 19.

As previously described, in the seventh exemplary embodiment, the control unit 6 executes the correction process of the threshold value K, similar to the sixth exemplary embodiment, the control unit 6 compares the corrected threshold value K with the output value E0 of the PM sensor 5 obtained before heating the sensor element 52, not with the output value E1 of the PM sensor 5 obtained at the first temperature in the sixth exemplary embodiment. This makes it possible to execute the failure detection process of the DPF under the condition in which the influence due to SOF has been eliminated.

Eighth Exemplary Embodiment

Next, a description will be given of the failure detection process according to the eighth exemplary embodiment of the present invention.

Hereinafter, a difference between the eighth exemplary embodiment and each of the exemplary embodiments previously described will be mainly explained. In the eighth exemplary embodiment, the control unit 6 executes the failure detection process which is different in process from that of each of the exemplary embodiments previously described. Other processes of the eighth exemplary embodiment are the same as the processes in each of the exemplary embodiments previously described. A description will now be given of the failure detection process according to the eighth exemplary embodiment.

Figure 20:
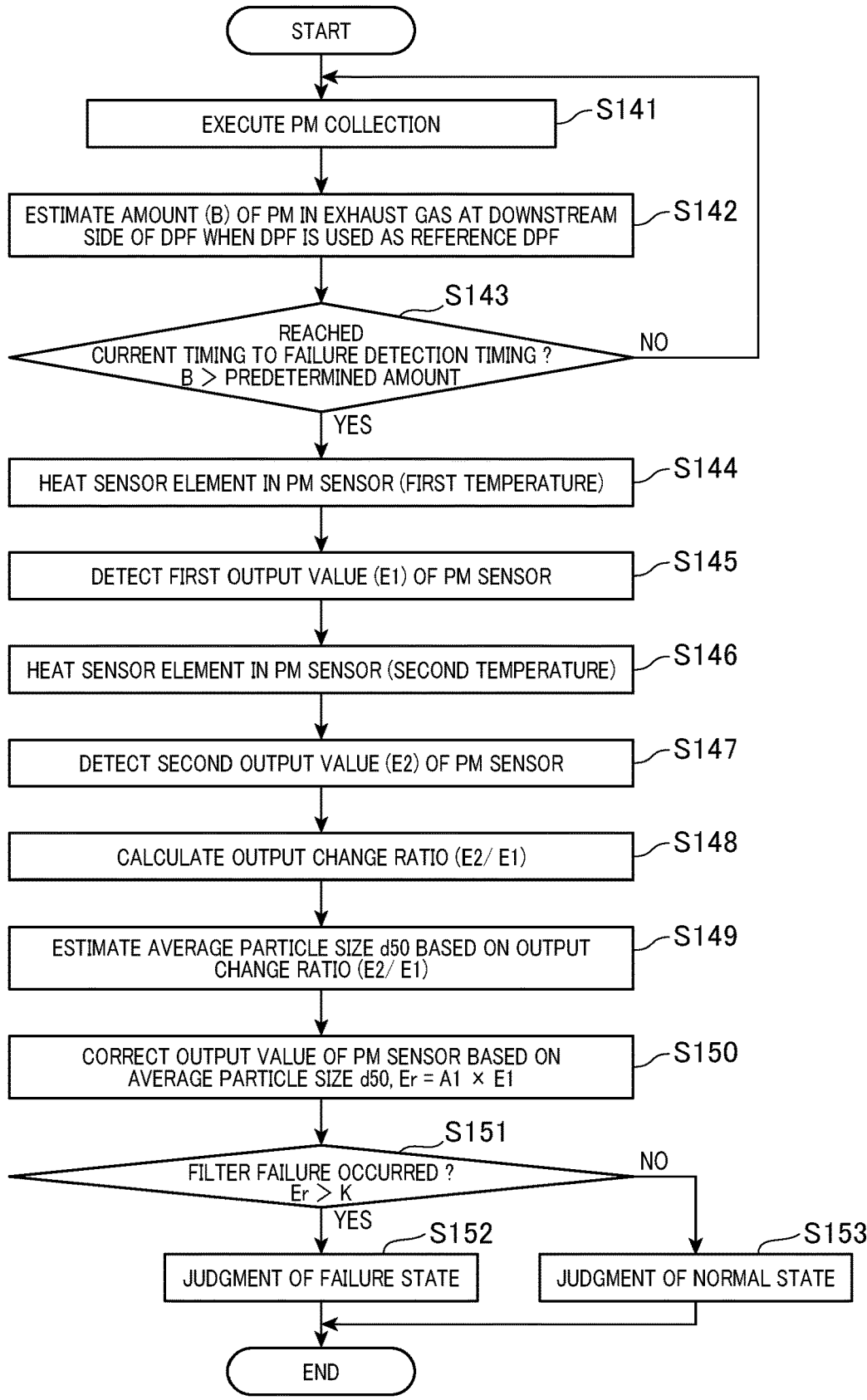
FIG. 20 is a view showing a flow chart of a failure detection process according to an eighth exemplary embodiment.

The control unit 6 executes, as the failure detection process, the processes in the flow chart shown in FIG. 20. The processes in step S142 and step S143 shown in FIG. 20 are different from the processes in step S62 and step S63 shown in FIG. 13. Other processes (step S141, step S144 to step S153) of the eighth exemplary embodiment are the same as the processes in step S61, step S64 to step S73 shown in FIG. 13. Further, the processes in step S142 and step S143 of the eighth exemplary embodiment are the same as the processes in step S42, step S43 shown in FIG. 12. Similar to the third exemplary embodiment, the control unit 6 according to the eighth exemplary embodiment estimates the accumulation amount B of PM which passes through the DPF 4 when the DPF 4 is uses as the reference DPF, and detects the failure detection timing on the basis of the estimated accumulation amount B of PM. The processes shown in FIG. 20 after the current timing reaches the failure detection timing are the same as the processes shown in FIG. 13. The failure detection process according to the eighth exemplary embodiment makes it possible to obtain the same effects of that of each of the exemplary embodiments previously described.

Ninth Exemplary Embodiment

Next, a description will be given of the failure detection process according to the ninth exemplary embodiment of the present invention.

Hereinafter, a difference between the ninth exemplary embodiment and the exemplary embodiments previously described will be mainly explained. In the ninth exemplary embodiment, the control unit 6 executes the failure detection process which is different in process from that of the exemplary embodiments previously described. Other processes of the ninth exemplary embodiment are the same as the processes in each of the exemplary embodiments previously described. A description will now be given of the failure detection process according to the ninth exemplary embodiment.

Figure 21:
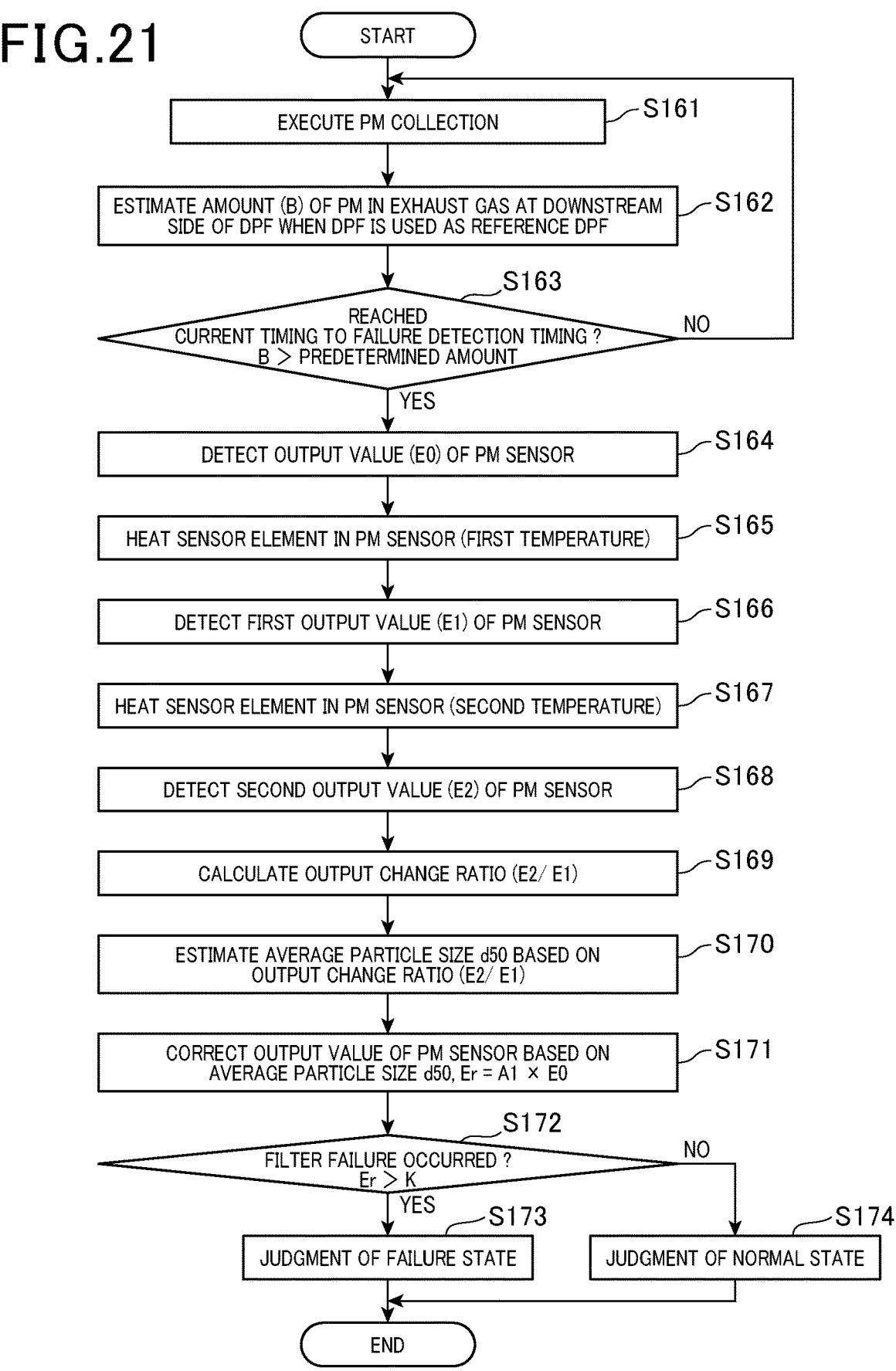
FIG. 21 is a view showing a flow chart of a failure detection process according to a ninth exemplary embodiment.

The control unit 6 executes, as the failure detection process, the processes in the flow chart shown in FIG. 21. The processes in step S162 and step S163 shown in FIG. 21 are different from the processes in step S82 and step S83 shown in FIG. 17. Other processes (step S161, step S164 to step S173) of the ninth exemplary embodiment are the same as the processes in step S81, step S84 to step S94 shown in FIG. 17. Further, the processes in step S162 and step S163 of the ninth exemplary embodiment are the same as the processes in step S42, step S43 shown in FIG. 12. Similar to the third exemplary embodiment, the control unit 6 according to the ninth exemplary embodiment estimates the accumulation amount B of PM which passes through the DPF 4 when the DPF 4 is uses as the reference DPF, and detects the failure detection timing on the basis of the estimated accumulation amount B of PM. The processes shown in FIG. 21 after the current timing has reached the failure detection timing are the same as the processes shown in FIG. 17. The failure detection process according to the ninth exemplary embodiment makes it possible to obtain the same effects of that of each of the exemplary embodiments previously described.

Tenth Exemplary Embodiment

Next, a description will be given of the failure detection process according to the tenth exemplary embodiment of the present invention.

Each of the exemplary embodiment previously described obtains the average particle size of PM, and corrects the output value of the PM sensor 5 and the threshold value, which is used in the failure detection process of detecting the failure of a DPF, on the basis of the obtained average particle size of PM. On the other hand, in the failure detection process according to the tenth exemplary embodiment, the control unit 6 calculates the amount of PM contained in exhaust gas on the basis of the average particle size.

Hereinafter, a difference between the tenth exemplary embodiment and the exemplary embodiments previously described will be mainly explained. Other processes of the tenth exemplary embodiment are the same as the processes in each of the exemplary embodiments previously described.

The failure detection device and the particle matter detection device according to the tenth exemplary embodiment has the same structure of those according to each of the exemplary embodiments previously described. However, the control unit 6 executes the failure detection process which is different from the failure detection process of each of the exemplary embodiments previously described. Specifically, the control unit 6 executes the processes in the flow chart shown in FIG. 22. The control unit 6 according to the tenth exemplary embodiment executes the processes shown in FIG. 22 in addition to, or instead of the failure detection process shown in each of FIG. 6, FIG. 10, FIG. 12, FIG. 13 and FIG. 17 to FIG. 22.

Figure 22:
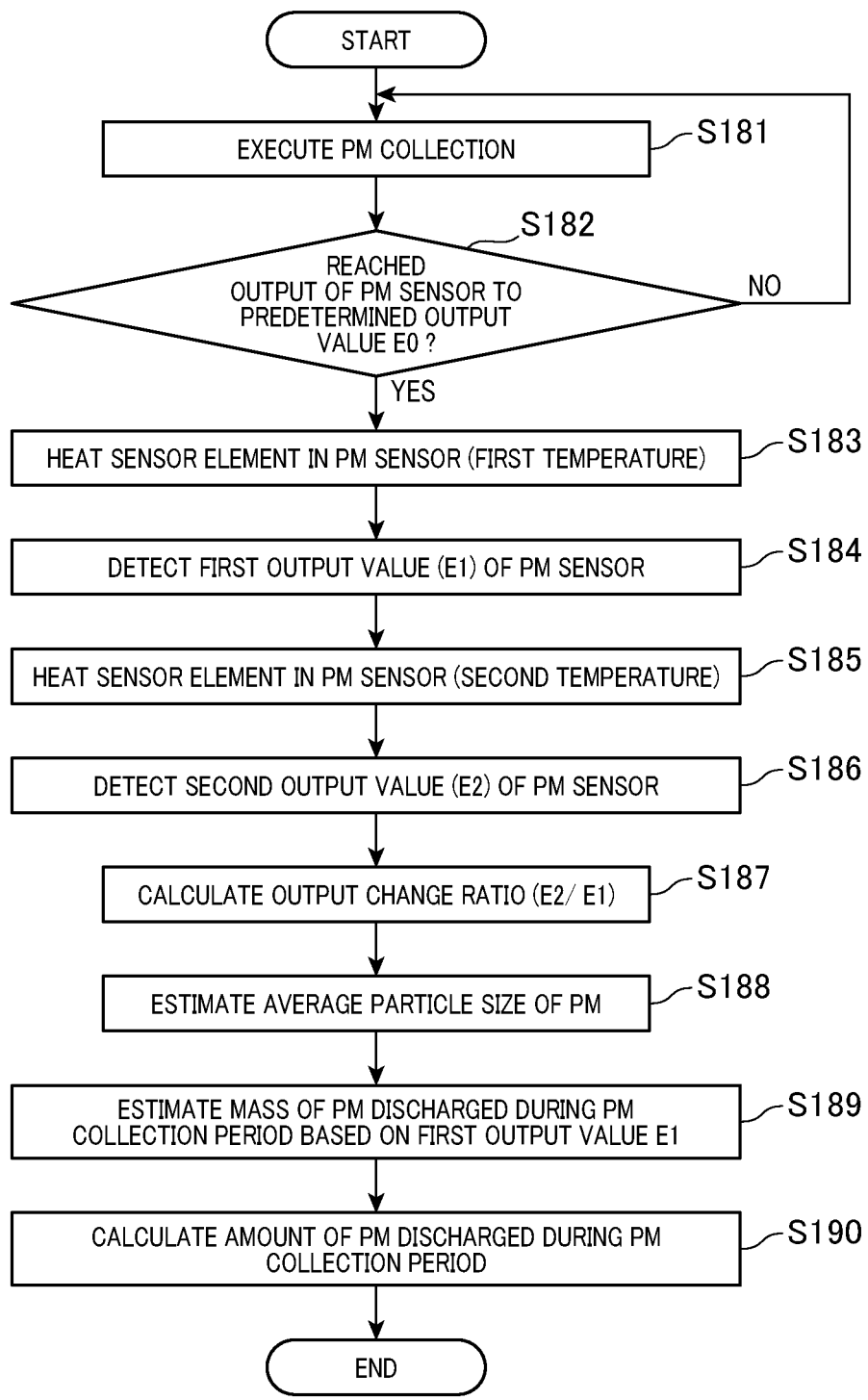
FIG. 22 is a view showing a flow chart of a failure detection process according to a tenth exemplary embodiment.

At the start of the failure detection process indicated by the flow chart shown in FIG. 22, the PM sensor 5 does not accumulate PM.

When starting the processes shown in FIG. 22, the control unit 6 executes the electrostatic collection of PM by using the PM sensor 5 (step S181). Next, the control unit 6 detects whether the output of the PM sensor 5 reaches the predetermined output value E0 of the PM sensor 5 (step S182). When the detection result indicates that he output of the PM sensor 5 does not reach the predetermined output value E0 of the PM sensor 5 ("NO" in step S182), the operation flow returns to step S181. The control unit 6 continues the execution of the electrostatic collection of PM and to monitor the output value of the PM sensor 5.

When the he output of the PM sensor 5 has reached the predetermined output value E0 of the PM sensor 5 ("YES" in step 182), the control unit 6 estimates the average particle size of PM (step S183 to step S188), similar to the processes in step S64 to step S69 shown in FIG. 13. That is, the control unit 6 estimates the average particle size of PM on the basis of the output change ratio E2/E1, wherein the output value E1 represents the output value of the PM sensor 5 at the first temperature at which SOF is evaporated, but soot does not burn, and the output value E2 represents the output value of the PM sensor 5 at the second temperature at which soot is burned.

Next, the control unit 6 estimates a mass of PM which have been discharged from the DPF 4 at the downstream side of the DPF 4 during the PM collection period (step S189), where the PM collection period is counted from the timing when the electrostatic collection process in step S181 is started to the timing when the output of the PM sensor 5 reaches the predetermined output value E0 (in other words, to the start timing when the heating of the sensor element 52 is started when a temperature of the sensor element 52 reaches the first temperature). This mass of PM represents the total mass of PM. The Pm sensor 5 generates and provides a value which correlates with the total mass of PM collected by the sensor element 53 in the PM sensor 5.

The mass of PM collected by the sensor element 52 correlates with the mass of PM which have been discharged to the downstream side of the DPF 4. That is, the output value of the PM sensor 5 correlates with the accumulation value of the mass of PM which have been discharged to the downstream side of the DPF 4 during the period counted from the timing when the PM sensor 5 starts to collect PM contained in exhaust gas to the timing when the PM sensor 5 outputs this output value.

When the relationship between the output of the PM sensor 5 and the mass of PM is detected in advance, it is possible for the control unit 6 to estimate the mass of PM has been discharged in the downstream side of the DPF 4 on the basis of the output of the PM sensor 5. At this time, it is possible for the control unit 6 to obtain the correct mass of PM, from which the influences due to SOF and a temperature of exhaust gas are eliminated, on the basis of the first output value E1 of the PM sensor 5 from which the influences due to SOF and a temperature of exhaust gas have been eliminated.

In order to estimate the mass of PM, the relationship between the output of the PM sensor 5 and the mass of PM contained in exhaust gas is detected in advance and stored in the memory 61. In this relationship, the larger the output of the PM sensor 5, the larger the mass of PM. In step S189, the control unit 6 estimates the mass of PM, which corresponds to the first output value E1, on the basis of the relationship stored in the memory 761.

In the processes shown in FIG. 22, the control unit 6 estimates the mass of PM after estimating the average particle size of PM. However, it is acceptable to execute the process in step S189 at any timing after the detection of the first output value E1 of the PM sensor 5.

Next, the control unit 6 calculates the amount of particulate matter particles, which have been discharged in the downstream side of the DPF 4 during the PM collection period, on the basis of the average particle size of Pm estimated in step S188 and the mass of PM estimated in step S189, and a predetermined specific gravity of PM (step S190). Specifically, the control unit 6 calculates an average volume of each PM, which have been discharged in the downstream side of the DPF 4 during the PM collection period. In more detail, the control unit 6 calculates the average volume of each PM by assigning the average particle size of PM to the following formula (1) under the assumption in which each PM has a spherical shape:

$$\text{Average volume} = 4/3\pi(D/2)^3 \qquad (1).$$

The control unit 6 calculates the amount of particulate matter particles by using the following formula (2) on the basis of the average volume, the mass and the specific gravity of PM. In the formula (2), the specific gravity of PM is determined in advance, specifically, the specific gravity of PM is 1 b/cm$^3$, for example. It is sufficient to store the specific gravity of PM into the memory 61. The term of (the average volume of PM×the specific gravity of PM) represents an average mass per PM which have been discharged in the downstream side of the DPF 4 during the PM collection period.

The amount of PM=mass of PM/(average volume of
PM×specific gravity of PM)        (2).

As previously described, according to the tenth exemplary embodiment, it is possible to obtain the amount of PM which have been discharged in the downstream side of the DPF 4 during the specific period of time (i.e. the PM collection period). This makes it possible for the control unit 6 to correctly execute the failure detection process of the DPF 4 on the basis of the amount of PM. In addition, because the control unit 6 estimates the amount of PM on the basis of the average particle size of PM, from which the influences due to SOF and a temperature of exhaust gas have been eliminated, this makes it possible to obtain the amount of PM with high accuracy and without the influences due to SOF and a temperature of exhaust gas.

Eleventh Exemplary Embodiment

Next, a description will be given of the failure detection process according to the eleventh exemplary embodiment of the present invention.

Hereinafter, a difference between the eleventh exemplary embodiment and each of the exemplary embodiments previously described will be mainly explained. In the eleventh exemplary embodiment, the control unit 6 calculates the amount of PM contained in exhaust gas on the basis of the average particle size of PM, like the tenth exemplary embodiment previously described.

Figure 23:
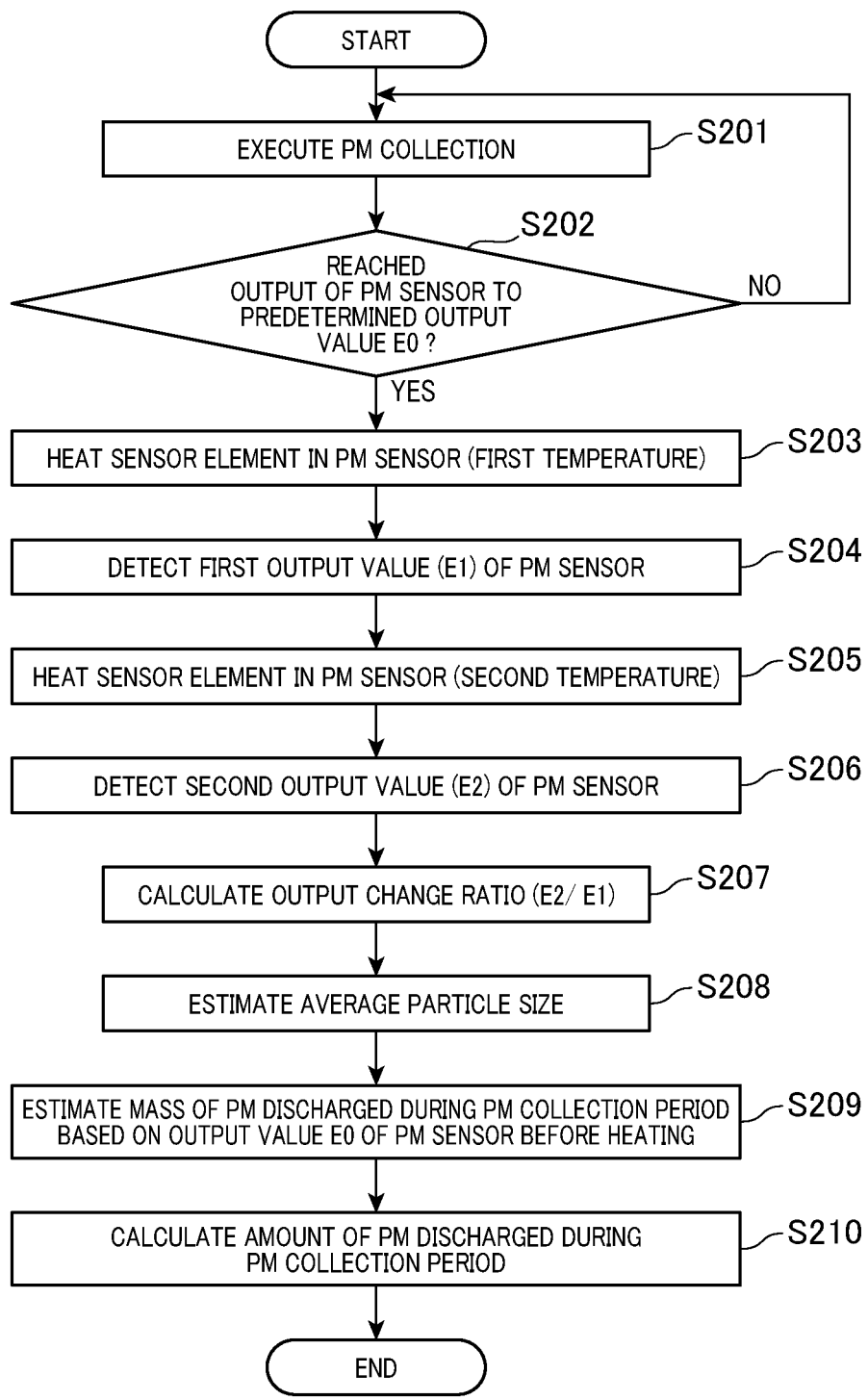
FIG. 23 is a view showing a flow chart of a failure detection process according to an eleventh exemplary embodiment.

The control unit 6 executes the processes shown in FIG. 23, instead of executing the processes shown in FIG. 22.

In FIG. 23, the process in step S209 is different from the process in step S189 shown in FIG. 22. Other processes (step S201 to step S208, step S210) shown in FIG. 23 are the same as the processes in step S181 to step S188, and step S190 shown in FIG. 22.

In step S189 shown in FIG. 22, the control unit 6 estimates the mass of PM on the basis of the first output value E1 of the PM sensor 5. On the other hand, in step S209 shown in FIG. 23, the control unit 6 estimates the mass of PM on the basis of the predetermined output value E0 of the PM sensor 5 before heating the sensor element 52 (in other words, at the start timing to heat the sensor element 52 to the first temperature). Specifically, the mass of PM, which corresponds to the predetermined output value E0 of the PM sensor 5, is detected in advance and stored in the memory 61. In step S209, it is sufficient for the control unit 6 to read the mass of PM stored in the memory 61. It is acceptable for the control unit 6 to execute the process in step S209 at any timing after the output of the PM sensor 5 has reached the predetermined output value E0 of the PM sensor 5.

As previously described, in the failure detection process according to the eleventh exemplary embodiment, the control unit 6 estimates the mass of PM on the basis of the output value E0 of the PM sensor 5 before heating the sensor element 52, and calculates the amount of PM on the basis of the estimated mass of PM. This makes it possible for the eleventh exemplary embodiment to obtain the same effects of the tenth exemplary embodiment.

Other Exemplary Embodiments

The concept of the present invention is not limited by the exemplary embodiments previously described and the scope of the claims. It is possible for the present invention to have the modifications without departing the concept of the present invention.

For example, in the first to ninth exemplary embodiments previously described, the control unit 6 executes one of the process of correcting the output of the PM sensor 5 and the process of correcting the threshold value. However, it is acceptable to execute both the processes. In this case, the control unit 6 executes the process in step S29 shown in FIG. 10 after the process in step S9 shown in FIG. 6 or before the process in step S9 shown in FIG. 6. A weighting value is determined, and the control unit 6 executes the process of correcting the output of the PM sensor 5 in step S9 by using the determined weight value, and also executes the process of correcting the threshold value in step S29 by using the determined weight value. For example, when the weighting value for the process of correcting the output of the PM sensor 5 is 0.7, and the weighting value for the process of correcting the threshold value is 0.3, the control unit 6 corrects the output of the PM sensor 5 by using the weighting value of 0.7 in step S9, and further corrects the threshold value by using the weighting value of 0.3 in step S29. Instead of executing the process in step S10 shown in FIG. 6, the control unit 6 detects whether the corrected output value Er of the Pm sensor 5 is more than the corrected threshold value Kr. This process makes it possible to provide the same effects of each of the exemplary embodiments previously described.

In the first to third exemplary embodiments previously described, the control unit 6 estimates the average particle size of PM on the basis of the output change ratio E2/E1. However, it is acceptable for the control unit 6 to estimate the average particle size of PM on the basis of the operation state (the rotation speed of the engine 2, the fuel injection amount, etc.) of the engine 2 because the average particle size of PM varies on the basis of the operation state of the engine 2. In this case, the relationship between the operation state of the engine 2 and the average particle size of PM has been detected in advance and stored in the memory 61. It is possible for the control unit 6 to estimate the average particle size of PM on the basis of the relationship stored in the memory 61 and the operation state of the engine 2.

Further, it is acceptable for the control unit 6 to estimate the average particle size of PM on the basis of the output change ratio E2/E1, where E2 represents the output value of the PM sensor 5 after heating the sensor element 52, and E1 represents the output value of the PM sensor 5 before heating the sensor element 52. In this case, the smaller the output change ratio E2/E1, the smaller the average particle size of PM. Similarly, in the fourth to eleventh exemplary embodiments, it is acceptable for the control unit 6 to estimate the average particle size of PM on the basis of the output change ratio E2/E1, where E2 represents the output value of the PM sensor 5 at the second temperature, and E1 represents the output value of the PM sensor 5 at the first temperature. In this case, the larger the output change ratio E2/E1, the smaller the average particle size of PM.

Still further, each of the exemplary embodiments previously described uses the PM sensor for detecting a failure of the DPF. However, it is acceptable to use the PM sensor for another purpose. For example, it is possible to arrange the PM sensor at the upstream side of the DPF so as to detect the amount of PM discharged from the engine 2. In this case, it is possible to detect an amount of PM with high accuracy, from which the influences due to the average particle size of PM have been eliminated, by correcting the output of the PM sensor.

In each of the exemplary embodiments previously described, the control unit 6 executes the failure detection process of the DPF on the basis of the comparison results between the estimated output value of the PM sensor and the actual output value of the PM sensor during the PM collection period, i.e. the electrostatic collection period. However, it is acceptable to execute the failure detection of the DPF on the basis of the slope of the output value of the PM sensor. Specifically, the control unit 6 estimates a slope in a change of the output value of the PM sensor when the DPF 4 is used as the reference DPF, and uses the estimated output change (slope) as the threshold value for the failure detection process. In this case, the actual output value of the PM sensor is compared with the threshold value. When the comparison result indicates that the actual output value of the PM sensor is more than the threshold value, the control unit 6 determines that the DPF has failed. On the other hand, when the comparison result indicates that the actual output value of the PM sensor is not more than the threshold value, the control unit 6 determines that the DPF is working correctly (is in a normal state). Similar to each of the exemplary embodiments, the control unit 6 corrects the actual output change and the threshold value on the basis of the average particle size of PM. This makes it possible to obtain the same effects of each of the exemplary embodiments previously described.

Figure 24:
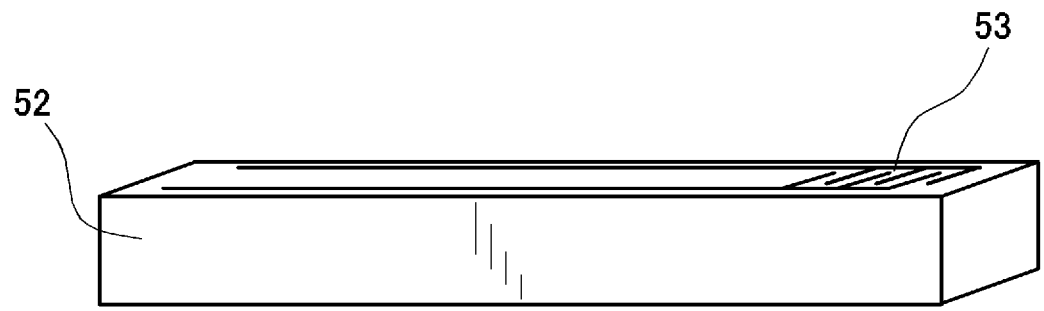
FIG. 24 is a view showing a structure of a sensor element in which opposing electrodes are formed on a surface extending a longitudinal direction of the sensor element.
Figure 25:
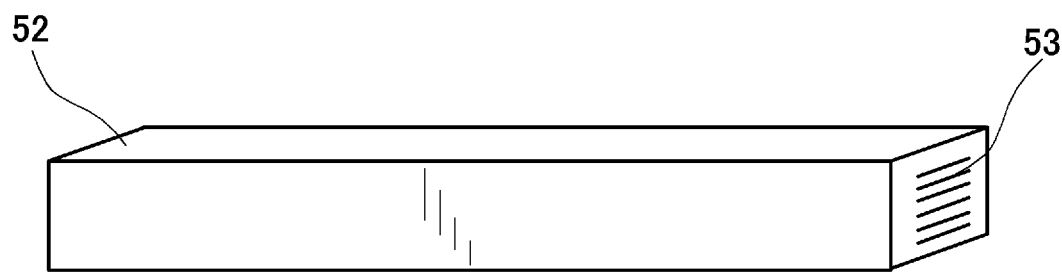
FIG. 25 is a view showing a structure of a sensor element in which opposing electrodes are formed on one side surface in the longitudinal direction of the sensor element.
Figure 26:
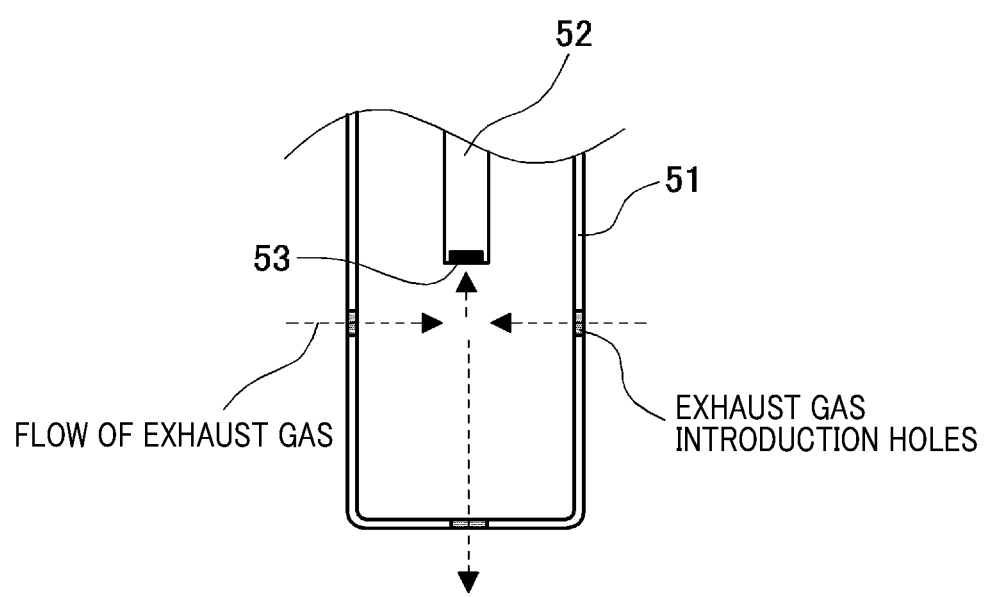
FIG. 26 is a view showing a PM sensor in which the sensor element shown in FIG. 25 is arranged in a cylindrical casing.

For example, the PM sensor used in each of the exemplary embodiments previously described has the structure in which the opposing electrodes 53 are formed along the longitudinal direction of the sensor element 24 on the surface of the sensor element 52 shown in FIG. 24, and the opposing electrodes 53 are faced to the side surface of the cover 51. However, it is possible for the PM sensor to have a structure shown in FIG. 25 or FIG. 26. That is, the opposing electrodes 52 are formed on one edge surface in the longitudinal direction of the sensor element 52 in the structure shown in FIG. 25. Still further, it is also acceptable for the PM sensor to have a structure shown in FIG. 26 in which the opposing electrodes 53 are faced to a front end side of the cover 51.

The control unit 6 and the memory 61 in each of the exemplary embodiments correspond to the particle size estimation section according to the present invention, wherein the control unit 6 executes the processes in step S4 to step S8, step S24 to step S28, step S44 to step S48, step S64 to step S69, step S85 to step S90, step S104 to step S109, step S125 to step S130, step S144 to step S149, step S165 to step S170, step S183 to step S188, and step S203 to step S208 shown in FIG. 6, FIG. 10, FIG. 12, FIG. 13, FIG. 17 to FIG. 23, respectively, and the memory unit 61 stores the relationship 100, 101 shown in FIG. 8 and FIG. 101, respectively.

Further, the control unit 6 corresponds to the failure detection section according to the present invention, wherein the control unit 6 executes the processes in step S2, step S3, step S10 to step S12, step S22, step S23, step S30 to step S32, step S42, step S43, step S50 to step S52, step S62, step S63, step S71 to step S73, step S82, step S83, step S92 to step S94, step S102, step S103, step S111 to step S113, step S122, step S123, step S132 to step S134, step S142, step S143, step S151 to step S153, step S162, step S163, step S172 to step S174 shown in FIG. 6, FIG. 10, FIG. 12, FIG. 13, FIG. 17 to FIG. 21, respectively.

Further, the control unit 6 corresponds to the correction section according to the present invention, wherein the control unit 6 executes the processes in step S9, step S29, step S49, step S70, step S91, step S110, step S131, step S150, and step S171 shown in FIG. 6, FIG. 10, FIG. 12, FIG. 13 and FIG. 17 to FIG. 21, respectively.

Further, the control unit 6 corresponds to the output estimation section according to the present invention, wherein the control unit 6 executes the processes in step S2, step S3, step S22, step S23, step S62, step S63, step S82, step S83, step S102, step S103, step S122 and step S123 shown in FIG. 6, FIG. 10, FIG. 13 and FIG. 17 to FIG. 19, respectively.

Further, the control unit 6 corresponds to the accumulation amount estimation section according to the present invention, wherein the control unit 6 executes the processes in step S42, step S43, step S142, step S143, step S162 and step S163 shown in FIG. 12, FIG. 20 and FIG. 21, respectively.

Further, the control unit 6 corresponds to the heating control section according to the present invention, wherein the control unit 6 executes the processes in step S5, step S25, step S45, step S64, step S66, step S85, step S87, step S104, step S106, step S125, step S127, step S144, step S146, step S165, step S167, step S183, step S185, step S203 and step S205 shown in FIG. 6, FIG. 10, FIG. 12, FIG. 13 and FIG. 17 and FIG. 23, respectively.

Further, the control unit 6 corresponds to the acquire section according to the present invention, wherein the control unit 6 executes the processes in step S4, step S6, step S7, step S24, step S26, step S27, step S44, step S46, step S47, step S65, step S67, step S68, step S86, step S88, step S89, step S105, step S107, step S108, step S126, step S128, step S129, step S145, step S147, step S148, step S166, step S168, step S169, step S184, step S186, step S187, step S204, step S206 and step S207 shown in FIG. 6, FIG. 10, FIG. 12, FIG. 13 and FIG. 17 to FIG. 23, respectively.

Further, the control unit 6 corresponds to the estimation section according to the present invention, wherein the control unit 6 executes the processes in step S8, step S28, step S48, step S69, step S90, step S109, step S130, step S149, step S170, step S188 and step S208 shown in FIG. 6, FIG. 10, FIG. 12, FIG. 13 and FIG. 17 and FIG. 23, respectively.

Further, the control unit 6 corresponds to the mass estimation section according to the present invention, wherein the control unit 6 executes the processes in step S189 and step S209 shown in FIG. 22 and FIG. 23, respectively.

Still further, the control unit 6 corresponds to the particle size calculation section according to the present invention, wherein the control unit 6 executes the processes in step S190 and step S210 shown in FIG. 22 and FIG. 23, respectively.

REFERENCE SIGNS LIST

1. Engine system,
2. Diesel engine (internal combustion engine),
3. Exhaust gas passage,
4. DPF (filter),
5. PM sensor (sensor),
6. Control unit, and
61. Memory.

The invention claimed is:
1. A particulate matter detection device comprises:
   a sensor, arranged between an internal combustion engine and an exhaust gas passage, providing an output value which corresponds to an amount of particulate matter contained in exhaust gas;
   a computer system, including a computer processor, the computer system at least be configured to perform:

a particle size estimation for estimating an average particle size of particulate matter contained in the exhaust gas; and a correction for correcting the output value of the sensor so that the amount of particulate matter increases according to reduction of the average particle size of particulate matter which has been estimated by the particle size estimation, wherein the sensor comprises:
a sensor element which collects particulate matter contained in exhaust gas; and
a pair of opposing electrodes which are arranged separated from each other on a surface of the sensor element;

wherein the sensor provides an output value which corresponds to a resistance value between the opposing electrodes;

wherein the sensor comprises a heater which generates heat energy to heat the sensor element, and wherein the computer system is further configured to perform:
a heat control which instructs the heater to heat the sensor element;
an acquisition which acquires an increased value which represents a gradient of the output value of the sensor when the heat control instructs the heater to heat the sensor element;
storage, in a memory, of a relationship between the increased value and the average particle size of particulate matter; and
an estimation which estimates the average particle size of particulate matter on the basis of the increased value acquired by the acquisition and the relationship stored in the memory; and
wherein the acquisition acquires, as the increased value, a change ratio of an output value of the sensor after heating to an output value before heating, wherein the output value of the sensor before heating represents an output value of the sensor before the heater heats the sensor element, and the output value of the sensor after heating represents an output value of the sensor which is increased after the heater heats the sensor element.

2. The particulate matter detection device according to claim 1, wherein the relationship between the increased value and the average particle size of particulate matter has been determined so that the average particle size of particulate matter reduces according to increasing of the change ratio of the output value of the sensor after heating to the output value of the sensor before heating.

3. The particulate matter detection device according to claim 1, wherein the acquisition acquires, as the output value of the sensor after heating, a peak value in output values of the sensor which rise by heating the sensor element.

4. A particulate matter detection device comprises:
a sensor, arranged between an internal combustion engine and an exhaust gas passage, providing an output value which corresponds to an amount of particulate matter contained in exhaust gas;
a computer system, including a computer processor, the computer system at least be configured to perform:
a particle size estimation for estimating an average particle size of particulate matter contained in the exhaust gas; and
a correction for correcting the output value of the sensor so that the amount of particulate matter increases according to reduction of the average particle size of particulate matter which has been estimated by the particle size estimation, wherein the sensor comprises:
a sensor element which collects particulate matter contained in exhaust gas; and
a pair of opposing electrodes which are arranged separated from each other on a surface of the sensor element;

wherein the sensor provides an output value which corresponds to a resistance value between the opposing electrodes;

wherein the sensor comprises a heater which generates heat energy to heat the sensor element, and wherein the computer system is further configured to perform:
a heat control which instructs the heater to heat the sensor element;
an acquisition which acquires an increased value which represents a gradient of the output value of the sensor when the heat control instructs the heater to heat the sensor element;
storage, in a memory, of a relationship between the increased value and the average particle size of particulate matter; and
an estimation which estimates the average particle size of particulate matter on the basis of the increased value acquired by the acquisition and the relationship stored in the memory;

wherein the heat control instructs the heater to heat the sensor element at a first temperature at which SOF is evaporated, and soot is not burned, and after this, the heat control instructs the heater to heat the sensor element at a second temperature at which soot is burned, and the acquisition acquires, as the increased value, a change ratio of a second output value of the sensor to a first output value of the sensor, wherein the first output value of the sensor represents the output value of the sensor at a timing when the heater heats the sensor element at the first temperature, and the second output value of the sensor represents the output value of the sensor at a timing when the heater heats the sensor element at the second temperature.

5. The particulate matter detection device according to claim 4, wherein the first temperature is within a range of not less than 200° C. and not more than 400° C.

6. The particulate matter detection device according to claim 4, wherein the second temperature is within a range of not less than 600° C. and not more than 1,000° C.

7. The particulate matter detection device according to claim 4, wherein the relationship is determined so that the average particle size of particulate matter is reduced according to increasing of the change ratio of the second output value of the sensor to the first output value of the sensor.

8. The particulate matter detection device according to claim 4, wherein the acquisition, as the second output value of the sensor, a peak value in output values of the sensor which rise by heating the sensor element to the second temperature.

9. The particulate matter detection device according to claim 4, wherein the computer system is further configured to perform:
a mass estimation section which estimates a mass of particulate matter contained in exhaust gas during a collection period counted from a timing when the sensor starts to collect particulate matter to a timing when the heater heats the sensor element to the first temperature; and a particle matter amount calculation which calculates the amount of particulate matter contained in exhaust gas during the collection period on the basis of the average particle size of particulate matter, the mass of particulate matter, and a specific gravity of particulate matter which has been determined in advance.

10. The particulate matter detection device according to claim 9, wherein the mass estimation estimates the mass of particulate matter on the basis of the first output value of the sensor.

11. The particulate matter detection device according to claim 9, wherein the mass estimation estimates the mass of particulate matter on the basis of the output value of the sensor at a timing when the heater starts to heat the sensor element to the first temperature.

12. The particulate matter detection device according to claim 10, wherein the specific gravity of particulate matter is 1 g/cm$^3$.

13. The particulate matter detection device according to claim 9, wherein the particle matter amount calculation calculates an average volume per particulate matter on the basis of the average particle size of particulate matter, and calculates the amount of particulate matter on the basis of the average volume and the specific gravity of particulate matter.

* * * * *